US011696943B2

(12) United States Patent
O'Neil et al.

(10) Patent No.: US 11,696,943 B2
(45) Date of Patent: Jul. 11, 2023

(54) SELF-ANTIGEN SPECIFIC T-CELLS AS VACCINES FOR AUGMENTING ENGRAFTMENT AND STABILITY OF AUTOLOGOUS TRANSFER

(71) Applicant: VANDERBILT UNIVERSITY, Nashville, TN (US)

(72) Inventors: Richard Thomas O'Neil, Nashville, TN (US); Matthew Hunter Wilson, Brentwood, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/964,007

(22) PCT Filed: Jan. 23, 2019

(86) PCT No.: PCT/US2019/014652
§ 371 (c)(1),
(2) Date: Jul. 22, 2020

(87) PCT Pub. No.: WO2019/147604
PCT Pub. Date: Aug. 1, 2019

(65) Prior Publication Data
US 2021/0030860 A1 Feb. 4, 2021

Related U.S. Application Data

(60) Provisional application No. 62/620,736, filed on Jan. 23, 2018.

(51) Int. Cl.
A61K 39/00 (2006.01)
A61K 39/02 (2006.01)
A61K 39/12 (2006.01)

(52) U.S. Cl.
CPC ............. A61K 39/02 (2013.01); A61K 39/12 (2013.01); A61K 2039/5156 (2013.01); A61K 2039/5158 (2013.01)

(58) Field of Classification Search
None
See application file for complete search history.

(56) References Cited

U.S. PATENT DOCUMENTS

2004/0241851 A1 12/2004 Askew et al.
2015/0079025 A1 3/2015 Wong et al.
2017/0158749 A1 6/2017 Cooper et al.
2017/0224798 A1 8/2017 Cooper et al.
2017/0240612 A1 8/2017 Bachmann et al.

OTHER PUBLICATIONS

Babitt JL & Lin HY (2012) Mechanisms of anemia in CKD. Journal of the American Society of Nephrology, 23(10):1631-1634.
Bear AS, Cruz CR, & Foster AE (2011) T cells as vehicles for cancer vaccination. Journal of biomedicine & biotechnology 2011:417403.
(Continued)

Primary Examiner — M Franco G Salvoza
(74) Attorney, Agent, or Firm — Meunier Carlin & Curfman LLC

(57) ABSTRACT

Disclosed are compositions and methods relating to genetically modified cells for the long-term expression of an antigen of interest.

Figures 1A, 1B:
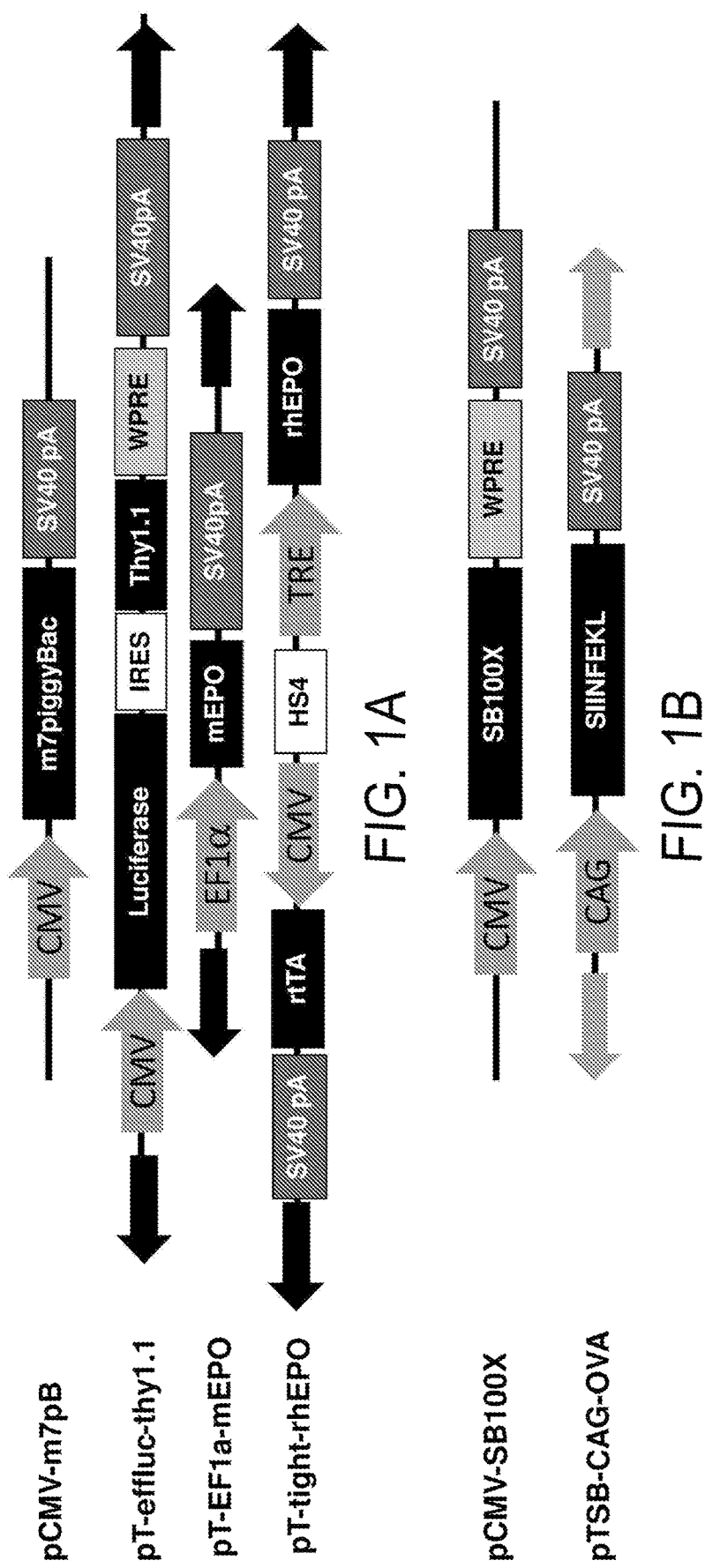

2 Claims, 15 Drawing Sheets
Specification includes a Sequence Listing.

(56) References Cited

OTHER PUBLICATIONS

Bertino P, et al. (2014) Vaccination with a piggyBac plasmid with transgene integration potential leads to sustained antigen expression and CD8(+) T cell responses. *Vaccine* 32(15):1670-1677.
Besarab A, et al. (1998) The effects of normal as compared with low hematocrit values in patients with cardiac disease who are receiving hemodialysis and epoetin. *N Engl J Med* 339(9):584-590.
Blum S, et al. (2017) TARGT Gene Therapy Platform for Correction of Anemia in End-Stage Renal Disease. *N Engl J Med* 376(2):189-191.
Clarke SR, et al. (2000) Characterization of the ovalbumin-specific TCR transgenic line OT-I: MHC elements for positive and negative selection. *Immunology and cell biology* 78(2):110-117.
Di Stasi A, et al. (2011) Inducible apoptosis as a safety switch for adoptive cell therapy. *N Engl J Med* 365(18):1673-1683.
Doherty JE, et al. (2012) Hyperactive piggyBac Gene Transfer in Human Cells and In Vivo. *Human Gene Therapy* 23(3):311-320.
Doherty JE, Woodard LE, Bear AS, Foster AF, & Wilson MH (2013) An adaptable system for improving transposon-based gene expression in vivo via transient transgene repression. *FASEB J.* 27(9):3753-3762.
Drueke TB, et al. (2006) Normalization of hemoglobin level in patients with chronic kidney disease and anemia. *N.Engl.J.Med.* 355(20):2071-2084.
Fesnak AD, June CH, & Levine BL (2016) Engineered T cells: the promise and challenges of cancer immunotherapy. *Nature reviews. Cancer* 16(9):566-581.
Foster AE, et al. (2008) Antitumor activity of EBV-specific T lymphocytes transduced with a dominant negative TGF-beta receptor. *Journal of immunotherapy* 31(5):500-505.
Galvan DL, et al. (2015) Anti-Tumor Effects after Adoptive Transfer of IL-12 Transposon-Modified Murine Splenocytes in the OT-I-Melanoma Mouse Model. *PLoS One* 10(10):e0140744.
Gao G, et al. (2004) Erythropoietin gene therapy leads to autoimmune anemia in macaques. *Blood* 103(9):3300-3302.
Heslop HE (2009) How I treat EBV lymphoproliferation. *Blood* 114(19):4002-4008.
Heslop HE, et al. (1996) Long-term restoration of immunity against Epstein-Barr virus infection by adoptive transfer of gene-modified virus-specific T lymphocytes. *Nat Med* 2(5):551-555.
Hoppe PS, Coutu DL, & Schroeder T (2014) Single-cell technologies sharpen up mammalian stem cell research. *Nature cell biology* 16(10):919-927.
Johnston J, et al. (2003) Regulated expression of erythropoietin from an AAV vector safely improves the anemia of beta-thalassemia in a mouse model. *Molecular therapy*, 7(4):493-497.
Kahlig KM, et al. (2010) Multiplexed transposon-mediated stable gene transfer in human cells. *Proceedings of the National Academy of Sciences of the United States of America* 107(4):1343-1348.
Kebriaei P, et al. (2016) Phase I trials using Sleeping Beauty to generate CD19-specific CAR T cells. *The Journal of clinical investigation* 126(9):3363-3376.
Koury MJ & Haase VH (2015) Anaemia in kidney disease: harnessing hypoxia responses for therapy. *Nature reviews. Nephrology* 11(7):394-410.
Mocini D, Leone T, Tubaro M, Santini M, & Penco M (2007) Structure, production and function of erythropoietin: implications for therapeutical use in cardiovascular disease. *Curr.Med.Chem.* 14(21):2278-2287.
Nakazawa Y, et al. (2009) Optimization of the PiggyBac transposon system for the sustained genetic modification of human T lymphocytes. *Journal of immunotherapy* 32(8):826-836.

Nakazawa Y, et al. (2013) Evaluation of Long-term Transgene Expression in piggyBac-Modified Human T Lymphocytes. *Journal of Immunotherapy* 36(1):3-10.
Osada S, et al. (1999) Gene therapy for renal anemia in mice with polycystic kidney using an adenovirus vector encoding the human erythropoietin gene. *Kidney Int* 55(4):1234-1240.
Pfeffer MA, et al. (2009) A trial of darbepoetin alfa in type 2 diabetes and chronic kidney disease. *N.Engl.J.Med.* 361(21):2019-2032.
Rooney CM, et al. (1998) Infusion of cytotoxic T cells for the prevention and treatment of Epstein-Barr virus-induced lymphoma in allogeneic transplant recipients. *Blood* 92(5):1549-1555.
Russo V, et al. (2007) Lymphocytes genetically modified to express tumor antigens target DCs in vivo and induce antitumor immunity. *The Journal of clinical investigation* 117(10):3087-3096.
Saridey SK, et al. (2009) PiggyBac Transposon-based Inducible Gene Expression In Vivo After Somatic Cell Gene Transfer. *Molecular Therapy* 17(12):2115-2120.
Scholler J, et al. (2012) Decade-long safety and function of retroviral-modified chimeric antigen receptor T cells. *Sci Transl Med* 4(132):132ra153.
Shapir N, et al. (2015) Preclinical and Preliminary Clinical Evaluation of Genetically Transduced Dermal Tissue Implants for the Sustained Secretion of Erythropoietin and Interferon alpha. *Human gene therapy. Clinical development* 26(4):216-227.
Skali H, et al. (2011) Stroke in patients with type 2 diabetes mellitus, chronic kidney disease, and anemia treated with Darbepoetin Alfa: the trial to reduce cardiovascular events with Aranesp therapy (TREAT) experience. *Circulation* 124(25):2903-2908.
Smith CA, et al. (1995) Production of genetically modified Epstein-Barr virus-specific cytotoxic T cells for adoptive transfer to patients at high risk of EBV-associated lymphoproliferative disease. *Journal of hematotherapy* 4(2):73-79.
Takacs K, et al. (2004) The regulated long-term delivery of therapeutic proteins by using antigen-specific B lymphocytes. *Proc Natl Acad Sci U S A* 101(46):16298-16303.
Woodard LE & Wilson MH (2015) piggyBac-ing models and new therapeutic strategies. *Trends Biotechnol* 33(9):525-533.
International Preliminary Report on Patentability issued for Application No. PCT/US2019/014652, dated Aug. 6, 2020.
International Search Report and Written Opinion dated Apr. 19, 2019, from International Application No. PCT/US2019/014652, 13 pages.
O'Neil, R.T. et al. "Transposon-modified antigen-specific T lymphocytes for sustained therapeutic protein delivery in vivo". Nature Communications, (2018), 9:1325.
Nakazawa, Y. et al. "PiggyBac-mediated Cancer Immunotherapy Using EBV-specific Cytotoxic T-cells Expressing HER2-specific Chimeric Antigen Receptor", The American Society of Gene & Cell Therapy, Molecular Therapy, vol. 19, No. 12, 2133-2143, Dec. 2011.
Russo, V. et al. "Lymphoctyes genetically modified to express tumor antigens target DCs in vivo and induce antitumor immunity", The Journal of Clinical Investigation, vol. 117, No. 10, Oct. 2007.
Kueberuwa, G. et al. "CCR7+ selected gene-modified T cells maintain a central memory phenotype and display enhanced persistence in peripheral blood in vivo", Journal for Immunotherapy of Cancer, (2017)5:14.
Mohammed, S. et al. "Improving Chimeric Antigen Receptor-Modified T Cell Function by Reversing the Immunosuppressive Tumor Microenvironment of Pancreatic Cancer", Molecular Therapy, vol. 25, No. 1, Jan. 2017.
Tsai, A. et al. "Producer T cells: Using genetically engineered T cells as vehicles to generate and deliver therapeutics to tumors", OncoImmunology, 2016, vol. 5, No. 5.

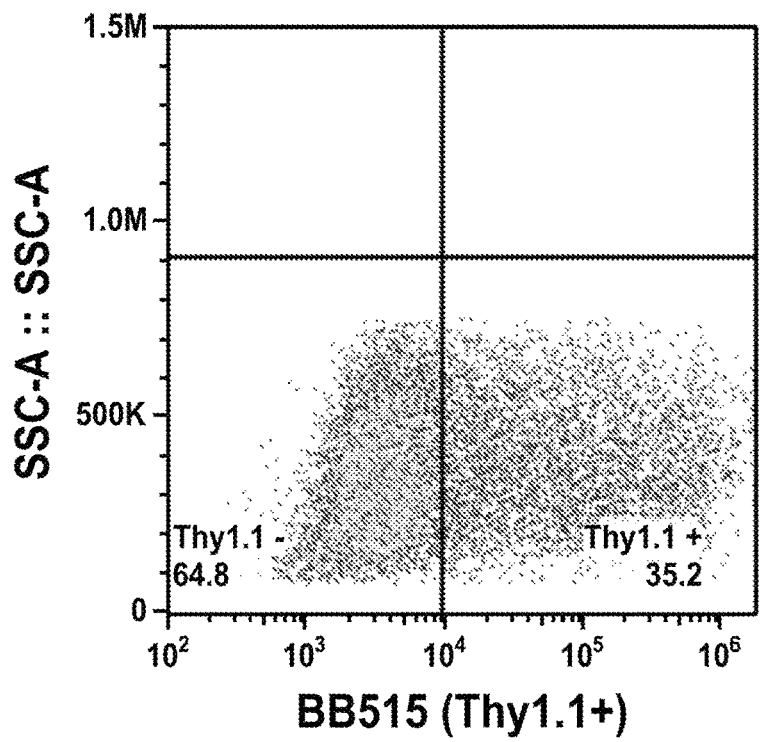
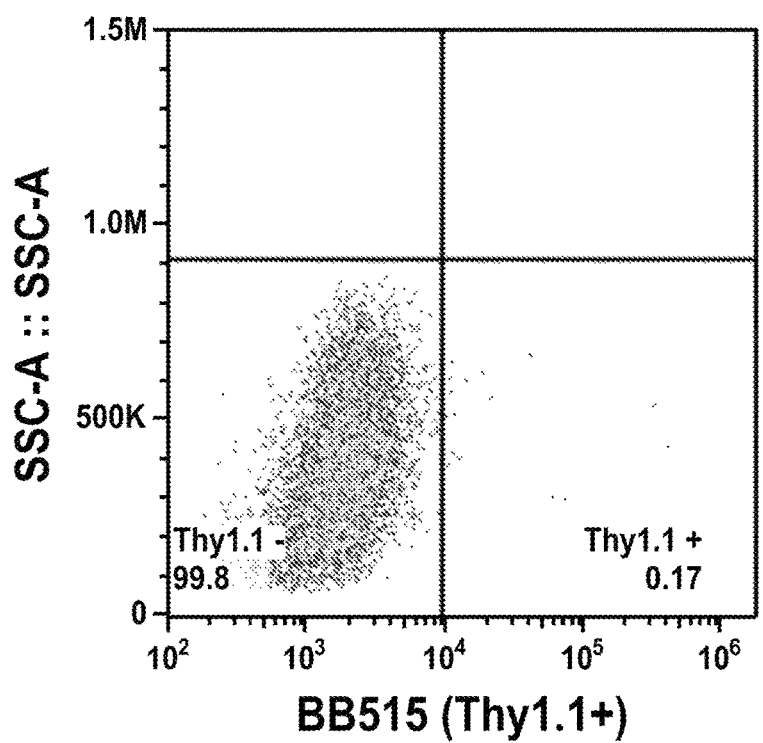
FIG. 2A

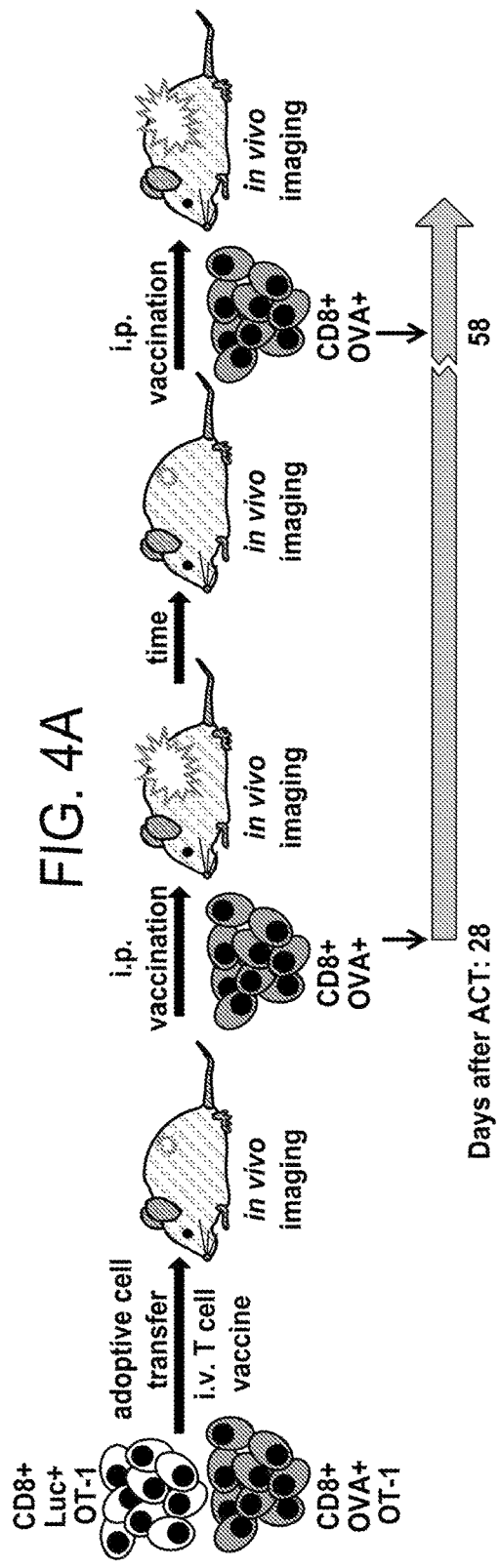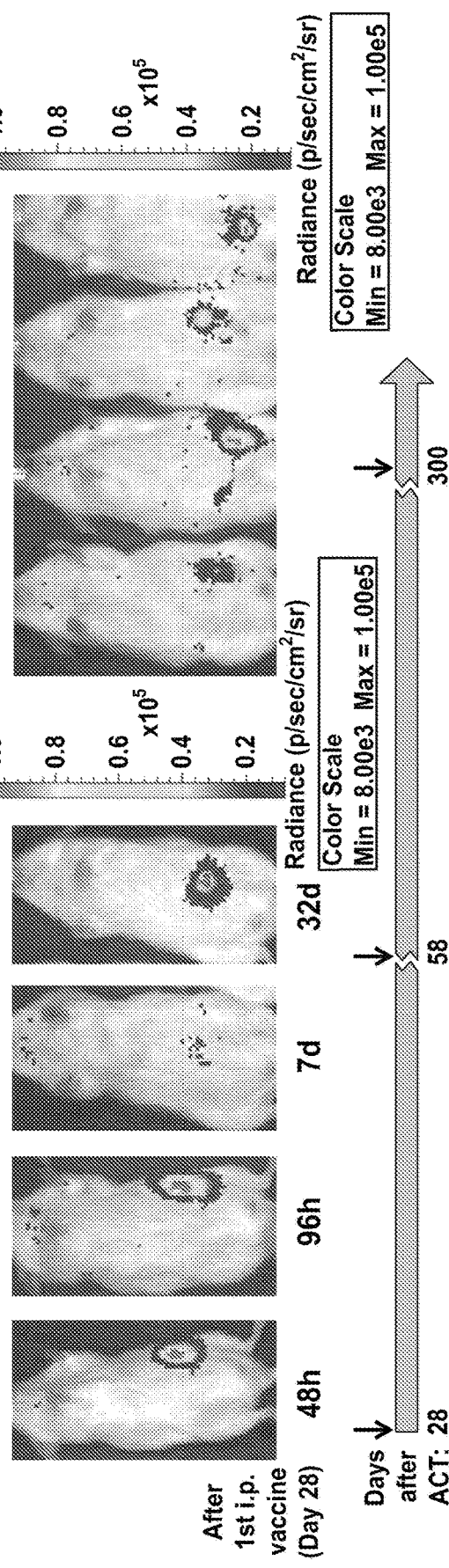

SEQUENCE LISTING

<160> NUMBER OF SEQ ID NOS: 2

<210> SEQ ID NO 1
<211> LENGTH: 44
<212> TYPE: DNA
<213> ORGANISM: Artificial Sequence
<220> FEATURE:
<223> OTHER INFORMATION: Synthetic Construct

<400> SEQUENCE: 1
gatcgccacc atgagtataa tcaactttga aaaactgtaa ccgg         44

<210> SEQ ID NO 2
<211> LENGTH: 8
<212> TYPE: PRT
<213> ORGANISM: Gallus gallus

<400> SEQUENCE: 2

Ser Ile Ile Asn Phe Glu Lys Leu
1               5

SELF-ANTIGEN SPECIFIC T-CELLS AS VACCINES FOR AUGMENTING ENGRAFTMENT AND STABILITY OF AUTOLOGOUS TRANSFER

This application claims the benefit of U.S. Provisional Application No. 62/620,736, filed on Jan. 23, 2018 which is incorporated herein by reference in its entirety.

This invention was made with government support under Grant No. DK093660 and DK114809 awarded by the National Institutes of Health and Grant No. BX002190 awarded by the Department of Veteran Affairs. The government has certain rights in the invention.

I. BACKGROUND

Adoptively transferred T-lymphocytes have recently been embraced as a therapeutic platform in oncology. A prerequisite for cell based adoptive transfer therapy is survival and effective engraftment of the therapeutic cells. Currently, effective engraftment of transferred T-lymphocytes is facilitated by a lympho-depleting preconditioning regimen which is also sometimes coupled with cytokine supplementation. This strategy relies primarily on the phenomenon of homeostatic proliferation of lymphocytes and on subsequent amplification of cells upon effective ligation of T-cell receptors or CARs. However, this strategy is limited by the attrition of adoptively transferred cells which typically results in engraftment of approximately 10% or less of transferred cells. What are needed are new methods to augment survival and expansion of transferred T cells.

II. SUMMARY

Disclosed are methods and compositions related to long-term presentation of an antigen of interest and methods of increasing T cell populations specific to said antigen.

In one aspect, disclosed herein are genetically modified T cells, wherein the T cell has been modified to express one or more T cell receptors specific for one or more antigens of interest and wherein the T cell further comprises one or more vectors encoding the one or more antigens of interest. In one aspect, the one or more antigens of interest can be a tumor antigen, viral antigen, bacterial antigen, or therapeutic peptide (such as, for example, a peptide hormone).

Also disclosed herein are genetically modified T cells of any preceding aspect, wherein the vector comprises a transposon system such as, for example, a sleeping beauty transposon system or PiggyBac transposon system. In one aspect, the antigen encoded by the vector can be operably linked to an inducible promoter or tissue specific promoter. Also disclosed are aspects, wherein the T cell further comprises an inducible knockout system for reducing transgene expression.

In one aspect, disclosed herein are methods of increasing engraftment of adoptively transferred T cells comprising administering to a subject a first T cell genetically modified to express a T cell receptor specific for an antigen of interest and a second T cell genetically modified to express a vector encoding the antigen of interest. In some aspects, the second T cell can comprise a T cell receptor specific for the antigen of interest being expressed by the vector.

Also disclosed herein are methods of providing long-term delivery of an antigen to a subject comprising administering to a subject a genetically modified T cell wherein the T cell has been modified to express an immunosuppressive cytokine, replacement enzyme, therapeutic peptide, or antigen of interest.

In some aspect, the T cell can be modified to express a T cell receptor specific for an antigen of interest, but lacking cytolytic function.

Also disclosed herein are methods of treating, inhibiting, or preventing a disease or condition such as cancer, a viral infection, a bacterial infection, chronic kidney disease, diabetes, or autoimmune disease (other autoimmune diseases like multiple sclerosis . . . described at the end) comprising administering to a subject with the disease or condition a genetically modified T cell wherein the T cell has been modified to express an T cell receptor or chimeric antigen receptor specific for an antigen of interest associated with the disease or condition and wherein the T cell comprises a vector encoding the antigen of interest.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A and 1B show vector schematics. FIG. 1A shows a schematic of the piggyBac transposase that was used with the pT-Tight-hEPO, pTPB-EF1α-mEPO, and pT-effluc-Thy1.1 transposons. FIG. 1B shows a schematic of the Sleeping Beauty transposase that was used with the pTSB-CAG-OVA transposon. CMV, cytomegalovirus immediate early enhancer/promoter; piggyBac, transposase; pA, SV40 polyadenylation signal; HS4E, core insulator sequence from the chicken B-globin 5'HS4 element; mEPO, recombinant murine erythropoietin cDNA; hEPO, recombinant human erythropietin cDNA; CAG, CAG synthetic promoter sequence; effluc, enhanced firefly luciferase; Thy1.1, mouse thy1.1 antigen; TRE, tetracycline response element, Tet-ON 3G, tetracycline transactivator; WPRE, woodchuck hepatitis post-transcriptional regulatory element; IRES, internal ribosomal entry site; SV40, simian virus 40 late polyadenylation signal. Solid arrows indicate inverted terminal repeat (ITR) sequences (black) piggybac ITRs (blue) Sleeping Beauty ITRs.

Figure 2B:
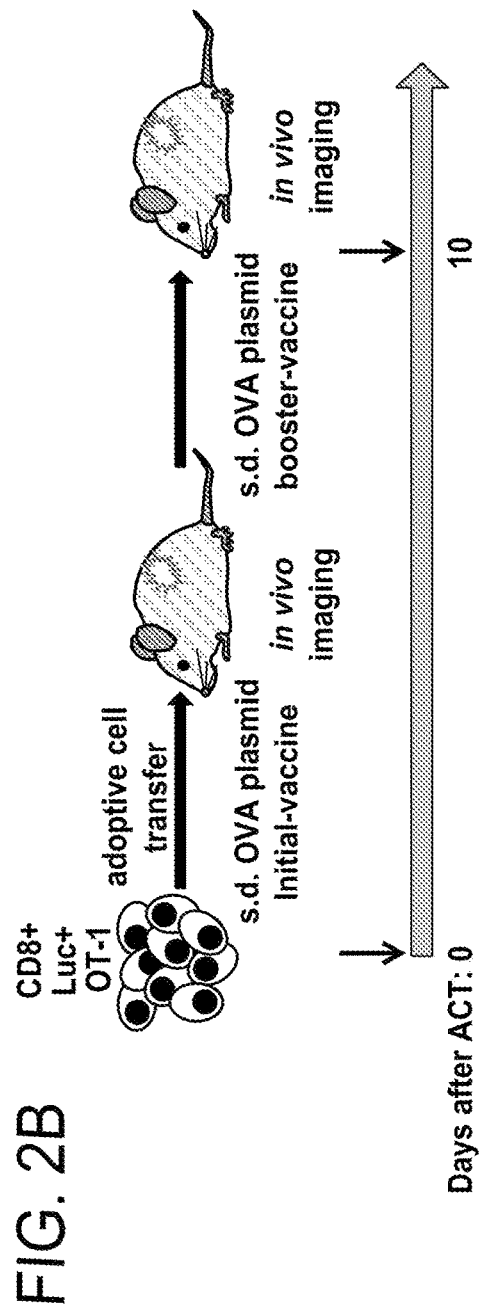
Figure 2C:
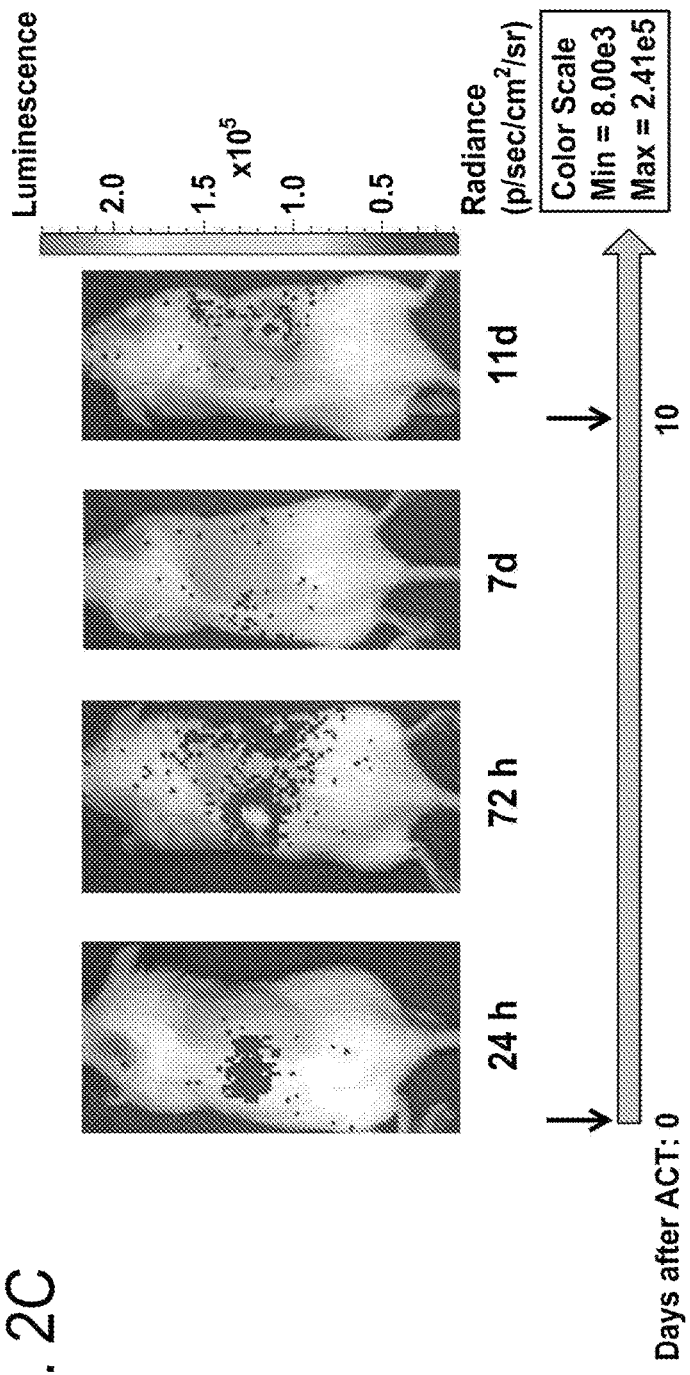

FIGS. 2A, 2B, and 2C show shows transposon modification and functional engraftment of OT-1 T cells. CD8+ T cells were modified with the pT-effluc-thy1.1 transposon and $1 \times 10^7$ CD8+ T cells were transferred into host mice. FIG. 2A shows representative flow cytometry analysis (from N=3) showing ~35% of T cells transfected with pT-effluc-thy1.1 plus pCMV-m7pB were thy1.1 positive after 24 hour culture post-transfection (top) compared to cells transfected with pTSB-CAG-OVA plus pCAG-SB100X (negative control) (bottom). FIG. 2B shows schematic representation of experimental design. FIG. 2C shows representative bioluminescent imaging (N=5) from a mouse subdermally injected with the pTSB-CAG-OVA plasmid vaccine immediately after adoptive cell transfer (ACT) and on day 10 after ACT. The blue arrow timeline arrow indicates the days after ACT. Red arrows indicate vaccine administration immediately after ACT and on day 10 after ACT. The images (a-d) correspond to the blue arrow timeline.

Figure 3A:
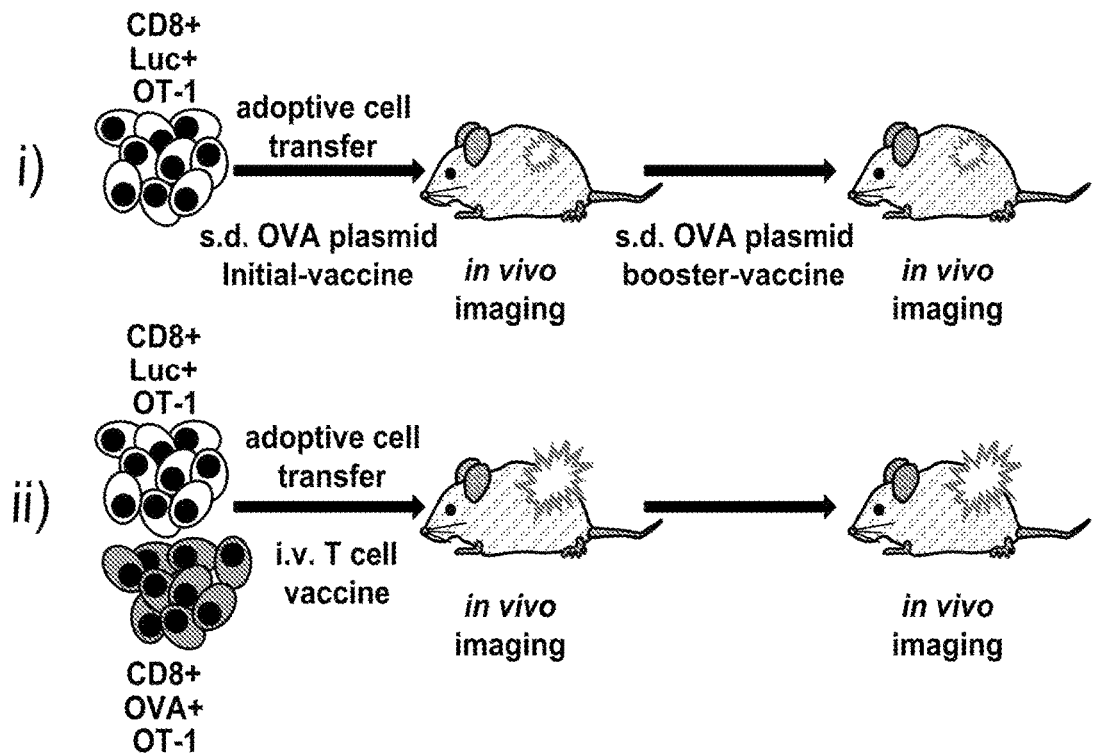
Figure 3B:
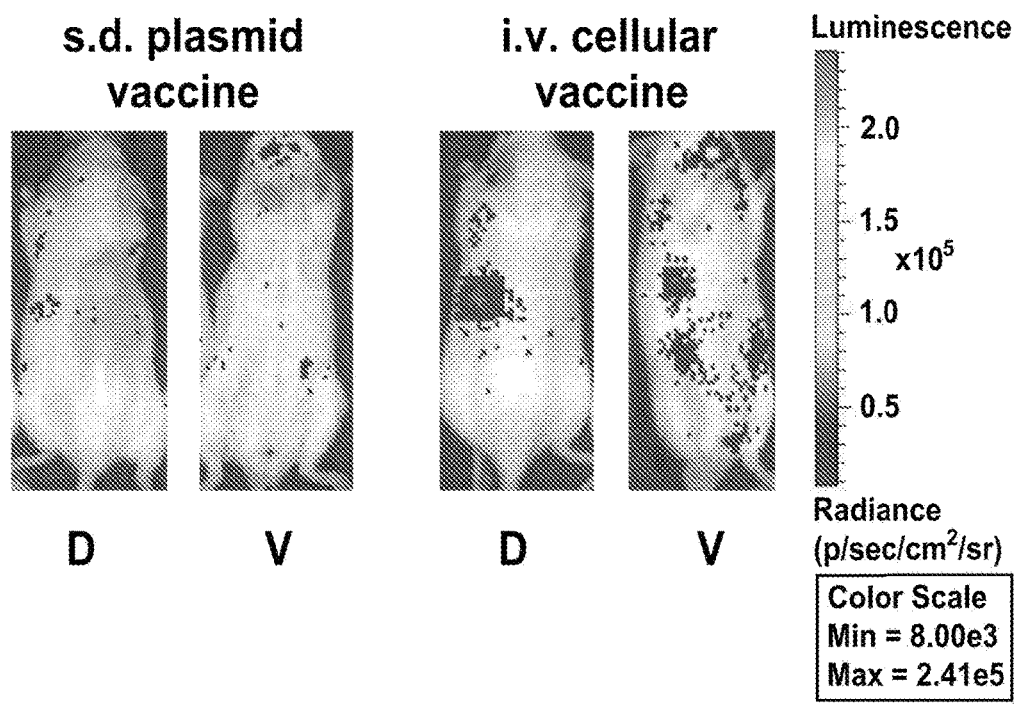
Figure 3C:
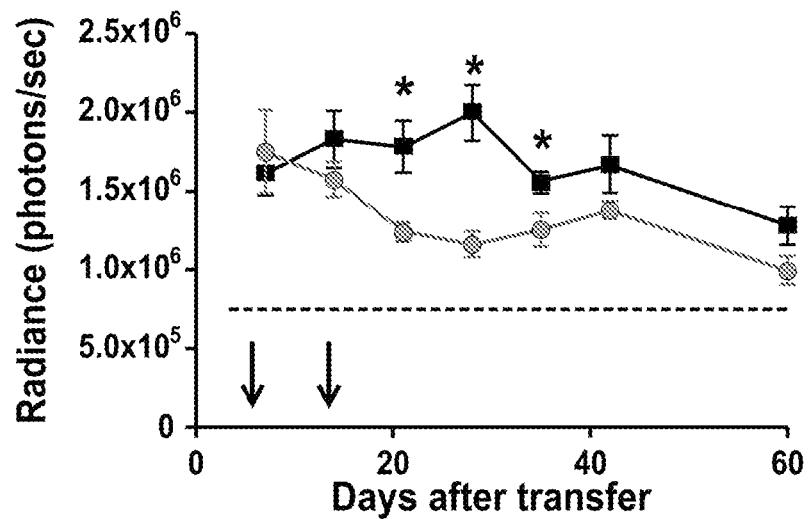
Figure 3D:
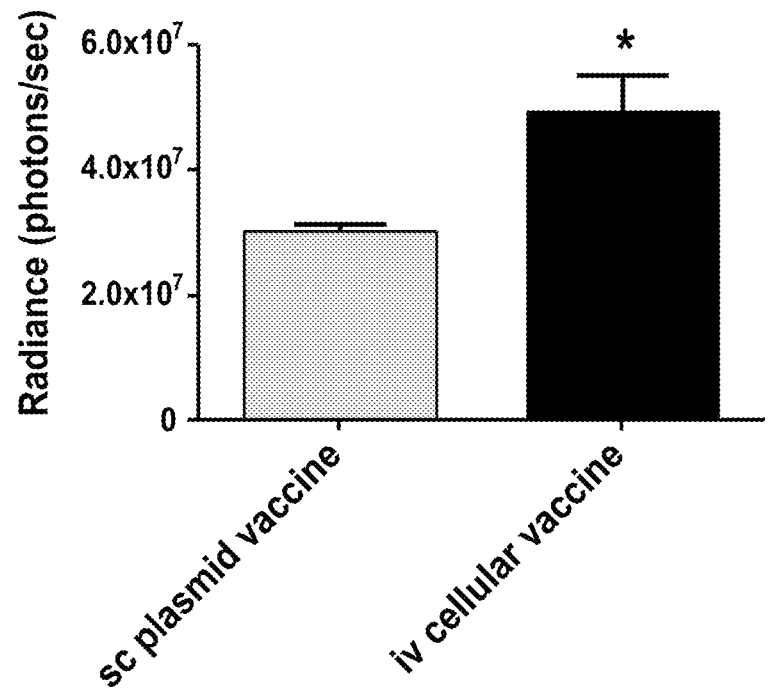

FIGS. 3A, 3B, 3C, and 3D show a comparison of vaccination approaches for augmenting T cell engraftment. Vaccination approaches for augmenting lymphocyte engraftment of were evaluated by infusing $1 \times 10^7$ CD8+ T cells genome modified with the pT-effluc-thy1.1 transposon. FIG. 3A shows a schematic representation of experiments comparing (i) subdermal vaccination (s.d.) and (ii) intravenous (i.v.) vaccination; yellow cells indicate T cells transfected with pT-effluc-thy1.1 and pCMV-m7pB, blue cells indicate vaccine T cells transfected with pTSB-CAG-OVA and pCMV-SB100X. FIG. 3B shows a representative bioluminescent images taken 21 days after iv transfer of $1 \times 10^7$ genome modified CD8+ T cells comparing the engraftment facilitated by a subdermal plasmid vaccine regimen (left panels) or an i.v. OT-1 T cell vaccine (D, dorsal; V, ventral) (N=5±SEM). FIG. 3C shows a plot showing total (dorsal+ventral) luciferase signals measured in mice that received either two subdermal plasmid vaccines at days 1 and 10 after transfer (red arrows), or a single i.v. OT-1 T cell vaccine concomitantly during autologous transfer. Dashed line indicates mean luminescence signal observed in mice injected with saline without d-luciferin. FIG. 3D shows a plot showing area under the curve for the sum total of the measurements presented in panel C. (N=5±SEM, *p<0.05)

FIGS. 4A, 4B, and 4C shows that cellular vaccine supports effective boosting and re-boosting. FIG. 4A shows a schematic representation of experimental protocol assessing cellular vaccine efficacy. FIG. 4B shows an i.p. booster vaccines were administered to mice receiving transfer of $1 \times 10^7$ pT-effluc-thy1.1 modified CD8+ T cells. The blue timeline arrow indicates the days after ACT. Red arrows indicate i.p. cellular vaccine administration on days 28, 58, and 298. A representative image (a-d) corresponds to the blue arrow timeline (N=5). FIG. 4C shows that effective boosting by i.p. T cell vaccine was observed 300 days (image, e, shown are 4 of the 5 mice) after ACT of $1 \times 10^7$ pT-effluc-thy1.1 modified cells co-administered with the i.v. OVA+OT-1 T cell vaccine.

Figure 5:
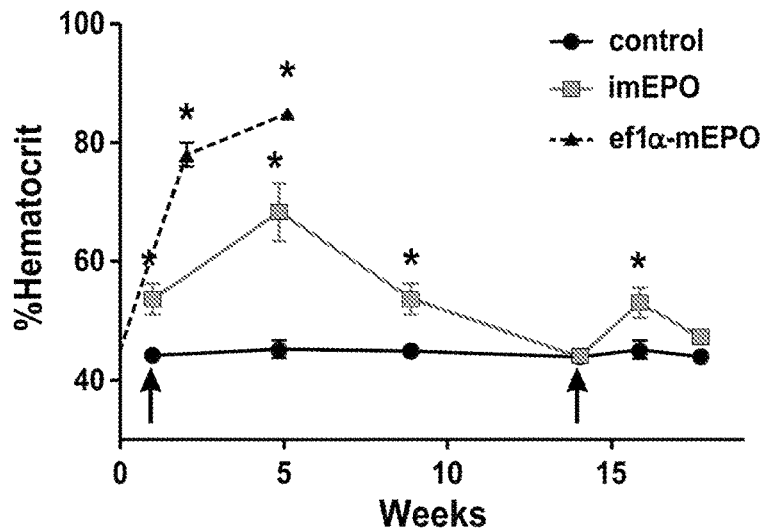

FIG. 5 shows the expression of mEPO from mouse liver. Hydrodynamic tail vein injection was used to deliver pCMV-m7pB (5 μg)+25 μg pT-EF1α-mEPO (ef1α-mEPO, dark triangles) or pT-Tight-mEPO (imEPO, red squares). Hematocrit was measured at the indicated timepoints. The black arrows indicate with 2 mg of doxycycline was given once via intraperitoneal injection. Control animals were untreated. (N=3±SEM; *, p<0.05 using student's T test compared to control).

Figure 6A:
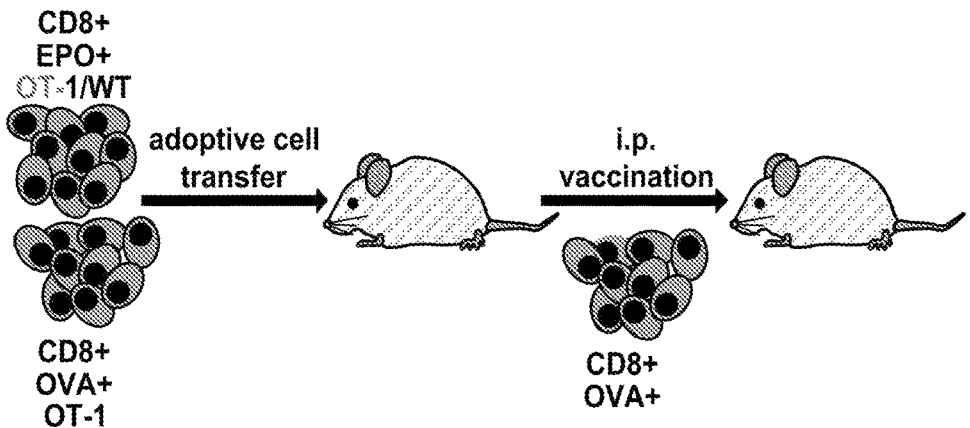
Figure 6B:
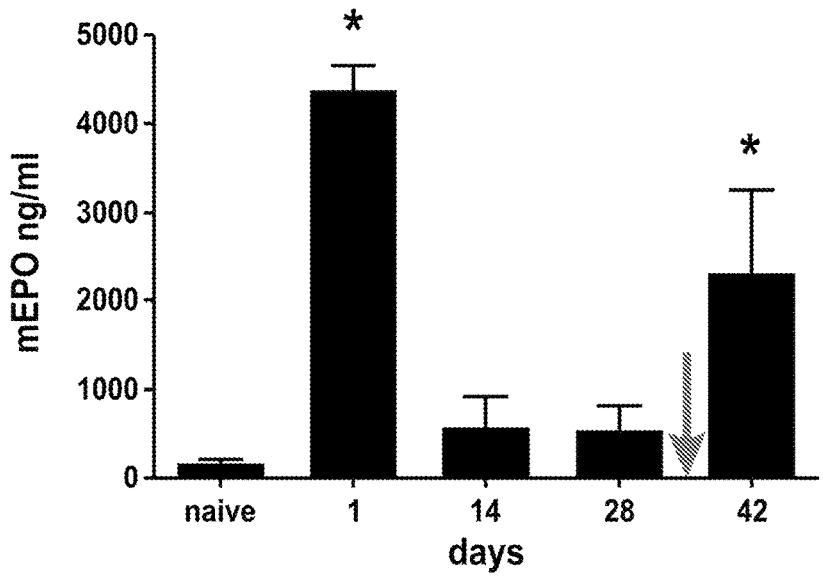
Figure 6C:
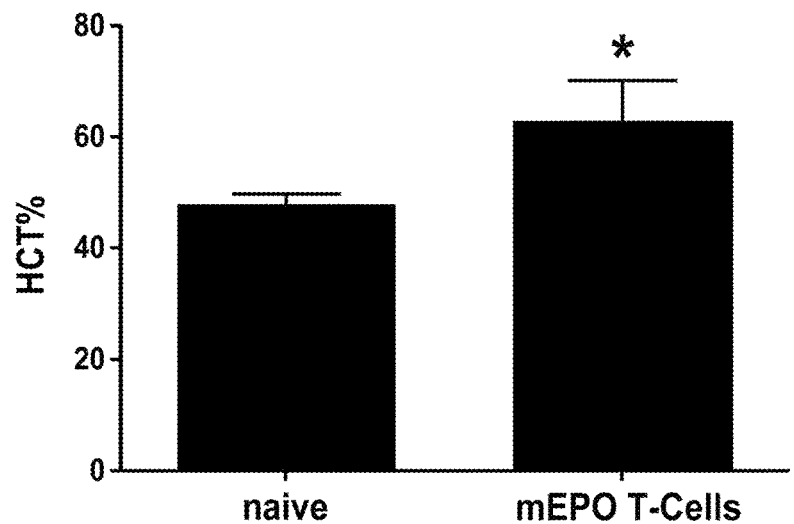

FIGS. 6A, 6B, and 6C show EPO delivery in vivo by EF1α-mEPO transposon modified T-lymphocytes. FIG. 6A shows a schematic representation of experiment evaluating ability of adoptively transferred transposon modified T-lymphoctes to produce EPO following adoptive cell transfer. FIG. 6B shows a graph of plasma EPO concentration in the days following ACT of 2×107 million EF1α-mEPO transposon modified T-lymphocytes. Statistical analysis was performed by comparing to pre-treatment levels using one way ANOVA with multiple comparisons (N=5±SEM). Red arrow indicates administration of cellular vaccine at day 41. FIG. 6C shows a graph comparing hematocrit 6 weeks after ACT (mice from panel B) to that of untreated control mice. The mean hematocrit of treated mice was 62.8±3.2 (N=5±SEM) and untreated mice was 47±1.4 (N=6±SEM), *p<0.05 using Student's T test.

Figure 7A:
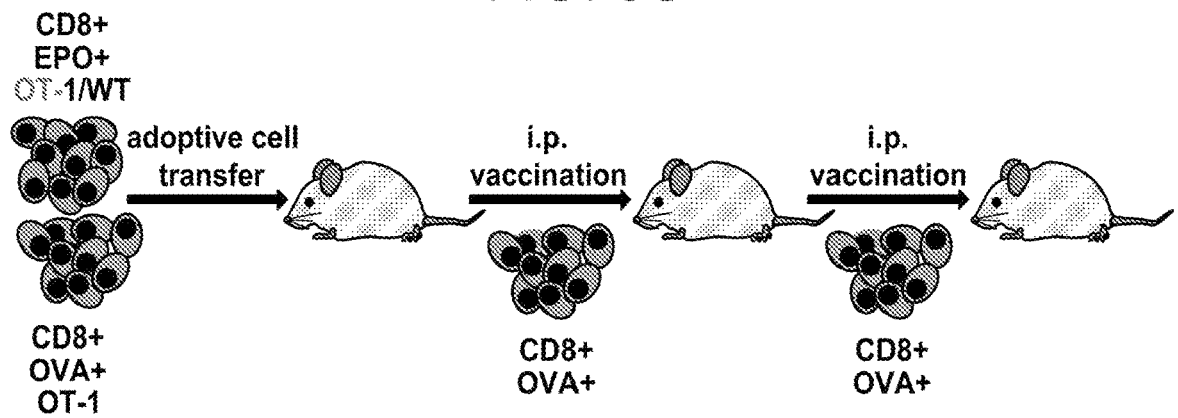
Figure 7B:
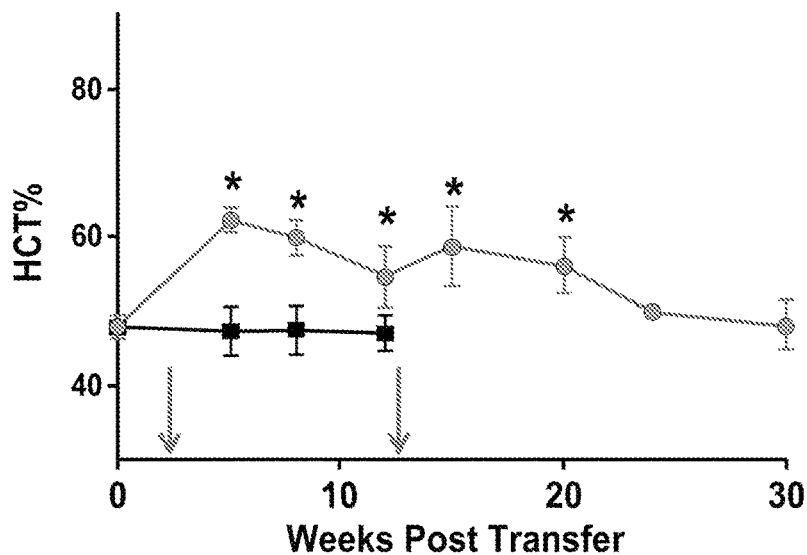
Figure 7C:
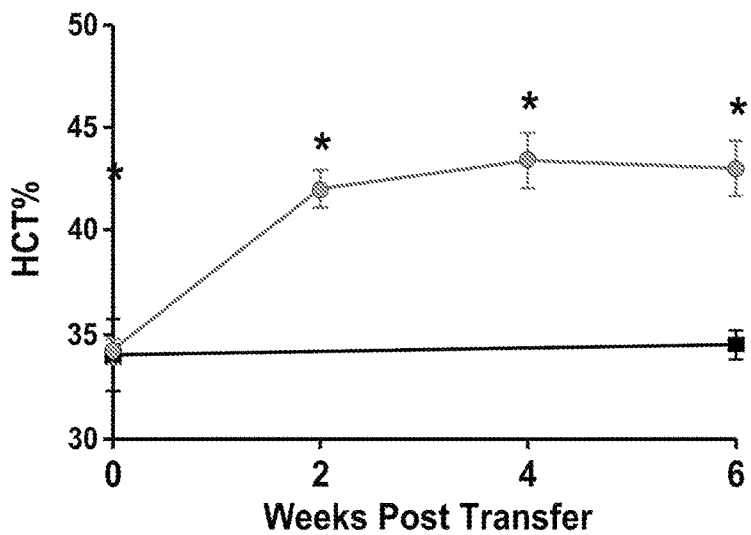

FIGS. 7A, 7B, and 7C show EF1α-mEPO transposon modified T-lymphocytes raise hematocrit in vivo. FIG. 7A shows a schematic representation of experiment evaluating ability of adoptively transferred transposon modified T cells to raise hematocrit in WT C57B16 mice. Red cells indicate OT-1 (red) or wild-type CD8+ T cells transfected with pT-ef1α-mEPO and pCMV-m7pB FIG. 7B shows a plot of mean hematocrit measurements observed in mice that received $2 \times 10^7$ pT-EF1α-mEPO genome modified wild-type T cells (black) or OT-1 T cells (red) and an i.v. OT-1 T cell vaccine. Additional i.p. T cell vaccines were administered (red arrow) on days 7 and 14, and then again on days 84 and 91 (OT-1 group) after initial transfer. Statistical analysis of hematocrit measurements were performed by comparing to pre-ACT levels (N=5±SEM, *p<0.01). The mean hematocrit for untreated mice was 47±1.4 (N=6±SEM). FIG. 7C shows a Plot of mean hematocrit measurements of mice subjected to adenine induced anemia. Mice treated with EF1α-mEPO transposon modified T-lymphocytes achieved a mean hematocrit>42 by 2 weeks post-ACT compared to a mean hematocrit of 34 for the untreated group. N=5±SEM for ACT treated (red) and N=3±SEM for untreated (black). *p≤0.05 using the Student's T test comparing treated to untreated groups at week 0 and 6.

Figure 8A:
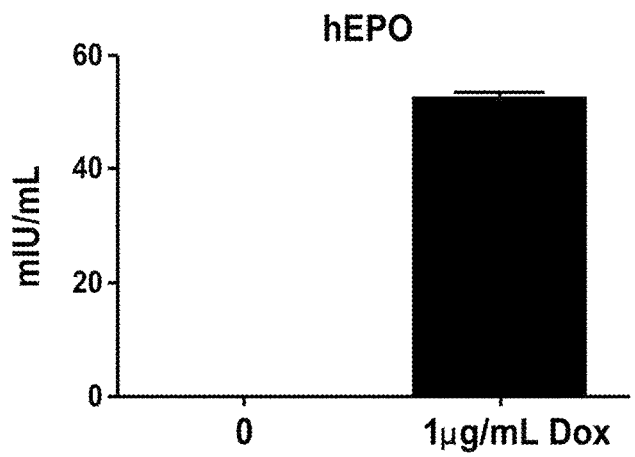
Figure 8B:
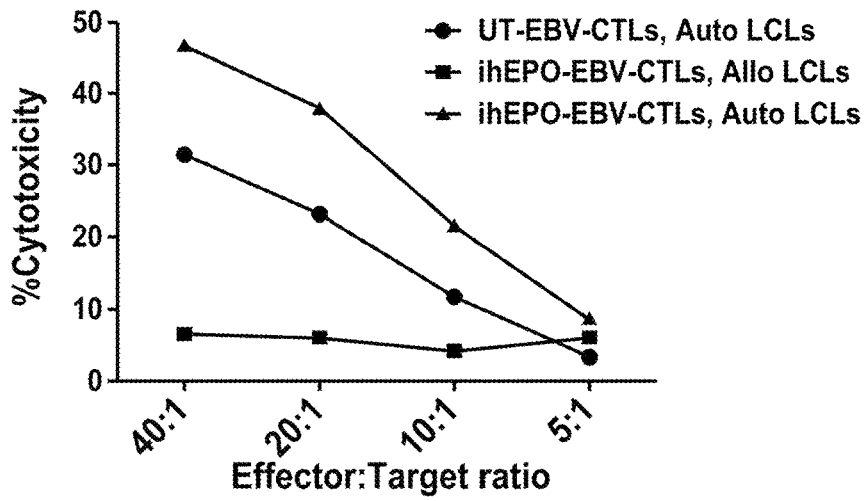

FIGS. 8A and 8B show regulated EPO production and retained target specificity of pT-Tight-hEPO modified EBV-specific T-lymphocytes. FIG. 8A shows genome modification of EBV-CTLs with pT-tight-hEPO results in tight regulation of EPO expression. FIG. 8B shows pT-tight-hEPO modified EBV-CTLs lyse target cells with similar efficiency as unmodified EBV-CTLs, indicating that genome modified EBV-CTLs retain target specificity. Untransfected EBV-CTLs (UT-EBV-CTLs) lysed autologous LCLs (Auto LCLs) as did EBV-CTLs transfected with pT-tight-hEPO (ihEPO-EBV-CTLs) with Auto LCLs. However, ihEPO-EBV-CTLs did not lyse allologous LCLs (Allo LCLs).

Figure 9:
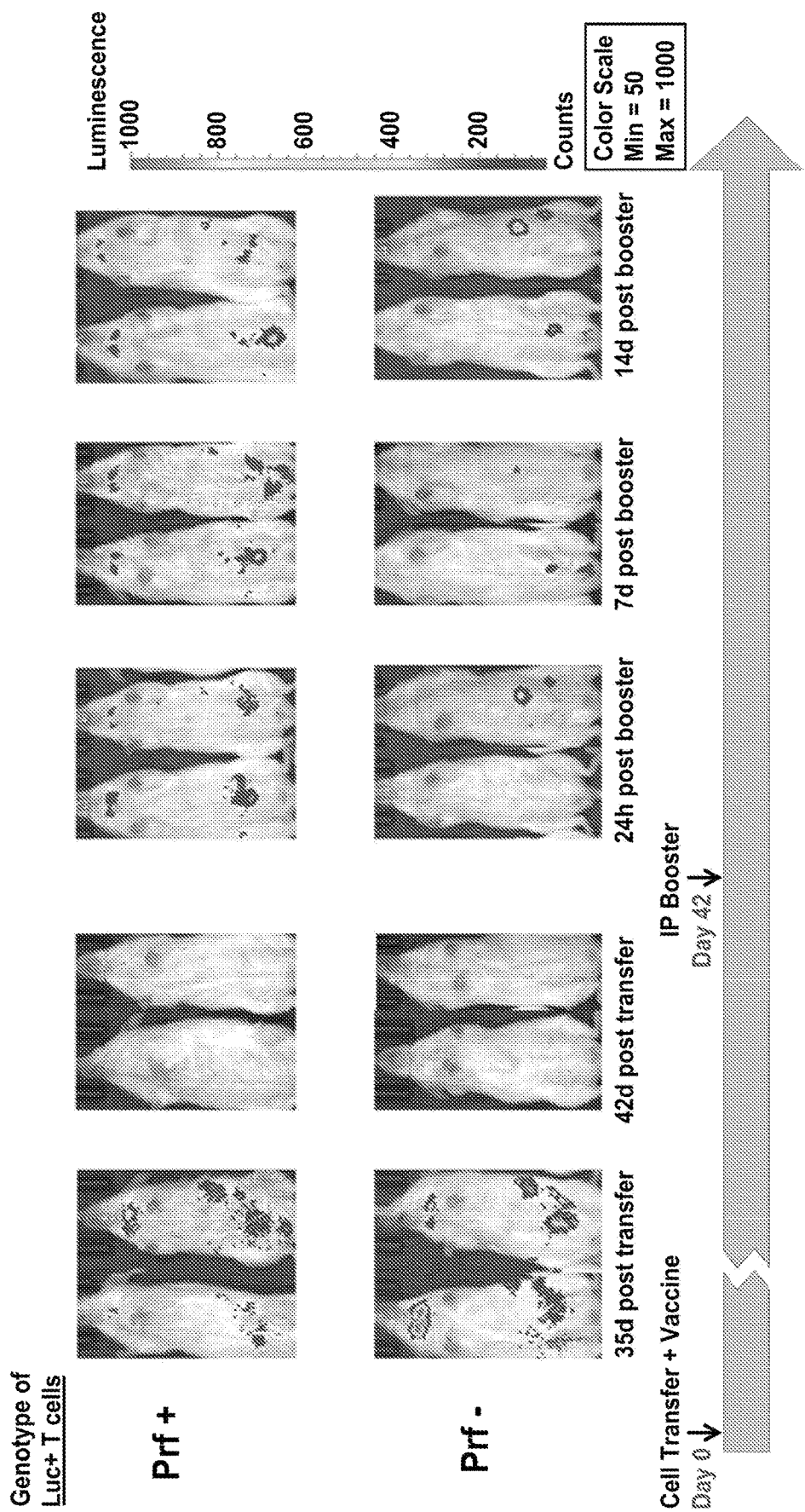

FIG. 9 shows that perforin mediated cytolytic function enhances antigen trafficking to lymph nodes (LNs).

Figure 10A:
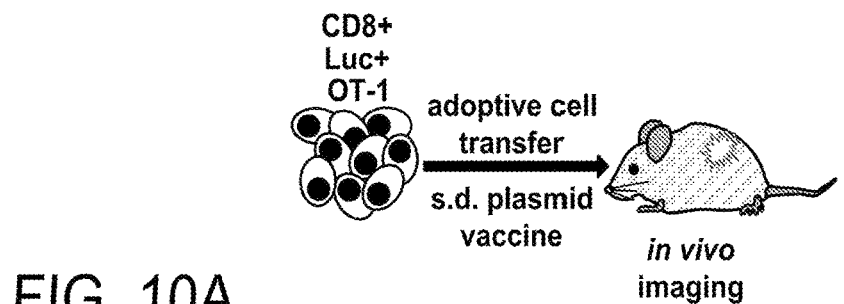
Figure 10B:
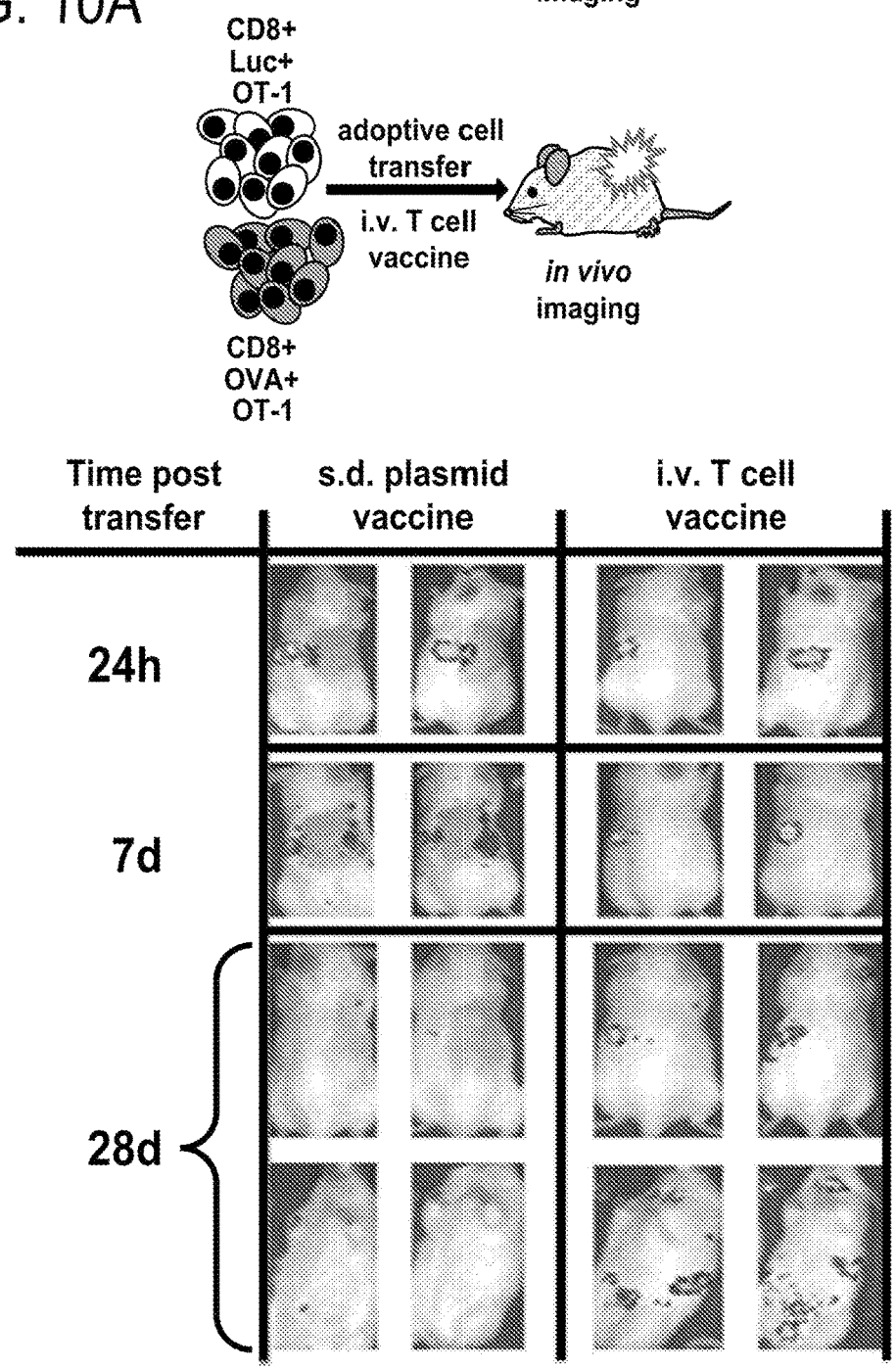

FIGS. 10A and 10B show Adoptive transfer of antigen-specific T cells augmented by cellular vaccine results in efficient long-term engraftment. FIG. 10A shows a schematic representation of each adoptive transfer approach-. FIG. 10B shows In vivo luciferase imaging showing efficient engraftment of engineered T cells. Plasmid vaccine: Adoptive transfer of 107 pT-EL-Thy1.1 modified OT1 T cells followed by subdermal plasmid vaccination with pT-CAG-OVA and pCMV-M7pB. T cell vaccine: Adoptive transfer of 107 pT-EL-Thy1.1 modified OT1 T cells concomitantly with 106 pT-CAG-OVA modified OT1 T cells.

Figure 11:
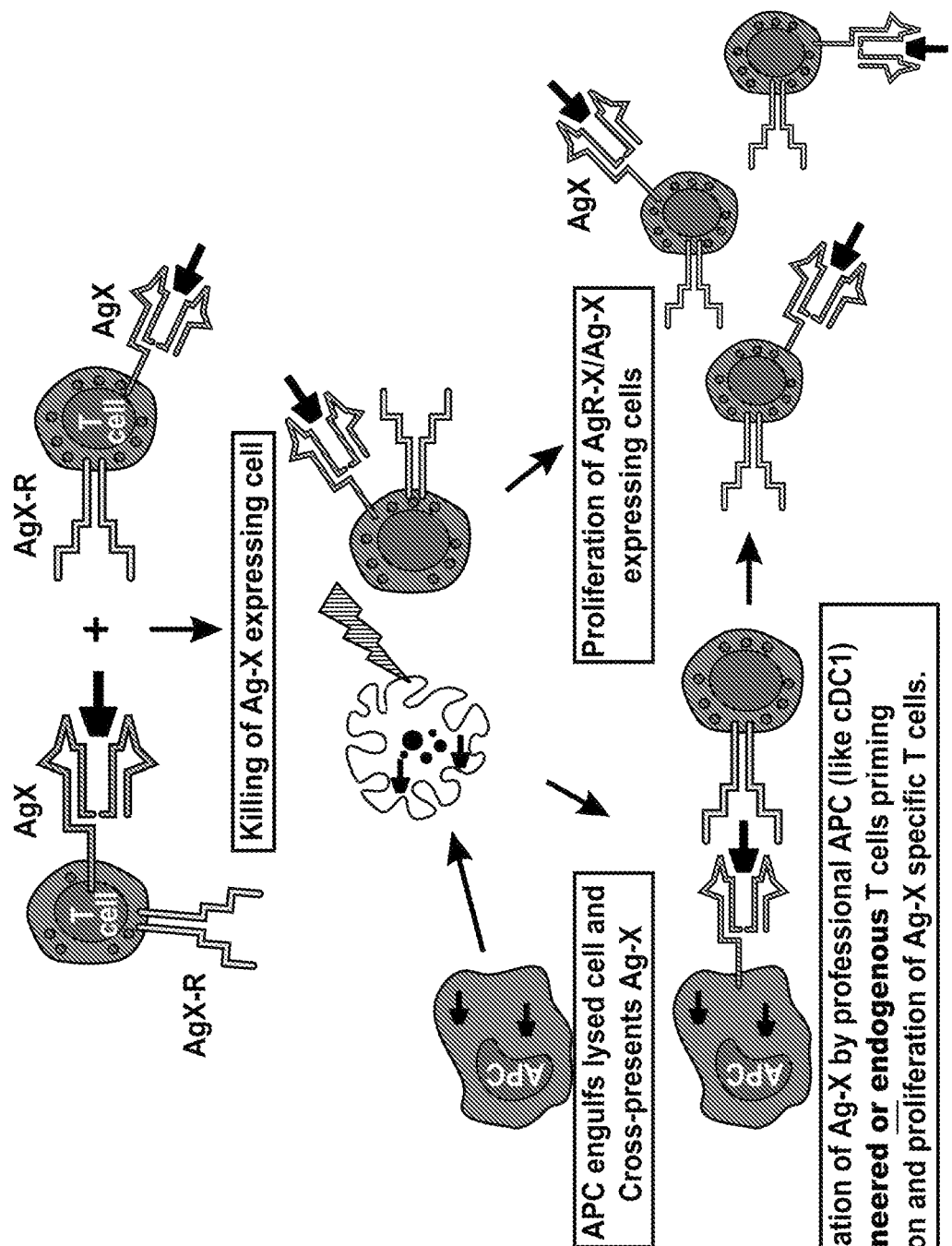

FIG. 11 shows a schematic representation of a T cell modified to express an antigen of interest and a T cell receptor specific for that antigen of interest and how said modified T cell can activate new antigen specific T cells and proliferate. AgX specific T cells are engineered to express AgX and used as a cellular vaccine to facilitate engraftment of AgX specific T cells.

Figure 12:
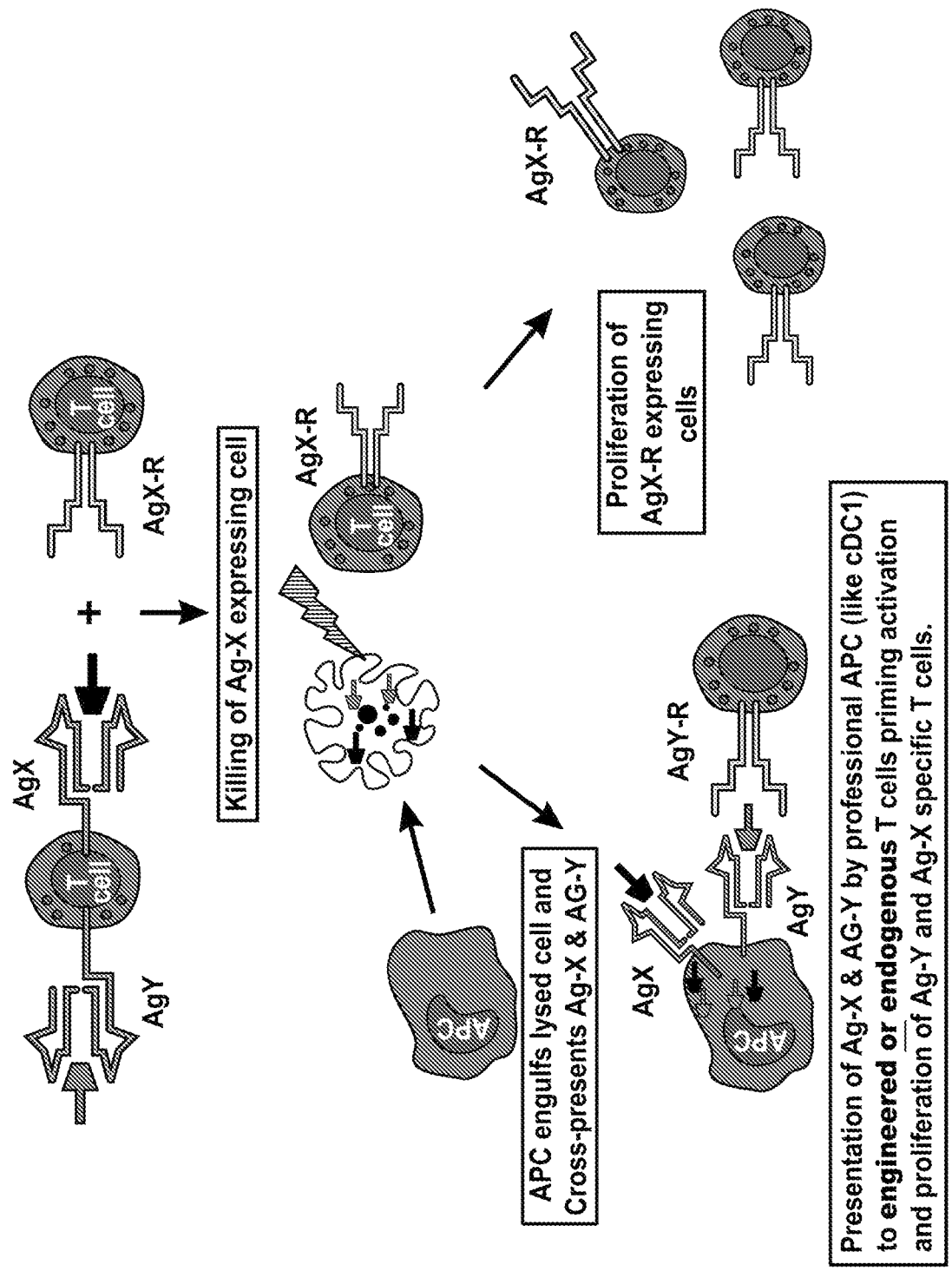

FIG. 12 shows a schematic representation of a T cell modified to express two different antigens of interest (a first antigen of interest and a second antigen of interest) and a second T cell modified to comprise receptor specific for one of the antigens of interest and how said receptor modified T cell can kill the antigen expressing T cell providing a source of the second antigen for antigen presenting cell uptake and endogenous T cell activation. As shown AgX specific T cells engineered to express AgX in addition to a AgY. The AgX expression mediates lysis of the T cells through the action of AgX specific T cells which promotes loading of tumor antigen onto dendritic cells for efficient priming of an antitumor response.

Figure 13:
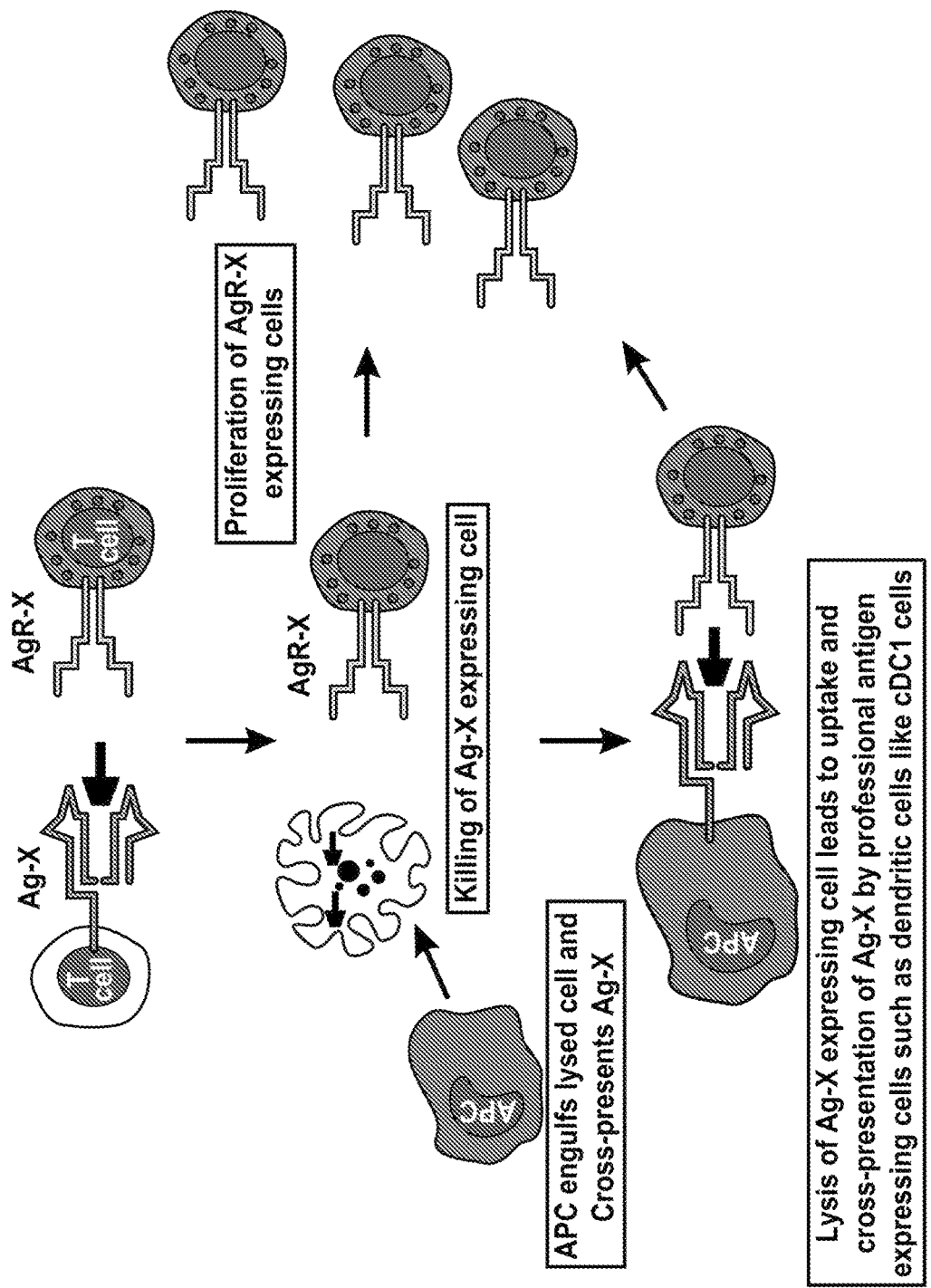

FIG. 13 shows a schematic representation of a schematic representation of a activation and proliferation of T cells through the co-transfection of one first T cell modified to express an antigen of interest and a second T cell modified to express a T cell receptor specific for that antigen of interest and how said modified T cells can activate new antigen specific T cells and proliferate. As shown, AgX expressing T cells are adoptively transferred along with another population of T cells that express the T cell receptor for AgX. Thus, the AgX expressing T cells are lysed and AgX is efficiently loaded onto dendritic cells leading to a more potent stimulation of both adoptively transferred and endogenous T cells that recognize AgX.

Figure 14:
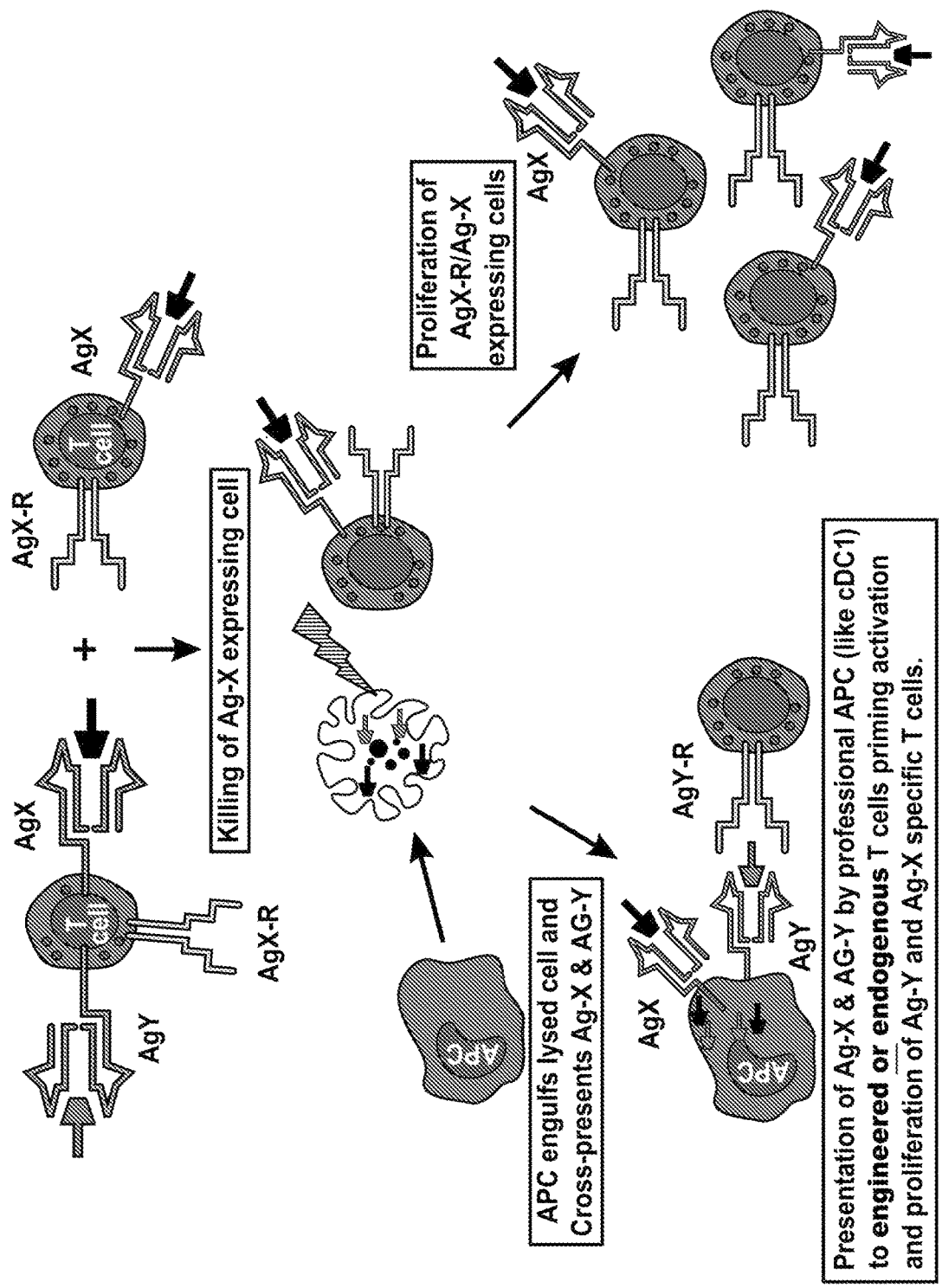

FIG. 14 shows a schematic representation of a schematic representation of a first T cell modified to express a first antigen of interest and a T cell receptor specific for that antigen of interest and how said modified T cell can be con-transfected with a second T cell modified to express the first antigen of interest and a second antigen of interest (optionally further being modified to comprise a T cell receptor specific for the first antigen of interest) and how said modified T cells can activate new antigen specific T cells and proliferate. As shown, T cells that have been selected for or engineered to specifically recognize AgX and also express AgX can be co-transferred with a second population of T cells that have been engineered to express AgX and AgY. The antigen AgX+AgY expressing T cells will then be targeted for lysis by the AgX antigen targeting T cells leading to enhanced uptake and cross-presentation of AgX and AgY by professional antigen presenting cells such as dendritic cells.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular genetically modified T cell (i.e., an SAS T cell) is disclosed and discussed and a number of modifications that can be made to a number of molecules including the genetically modified T cell (i.e., an SAS T cell) are discussed, specifically contemplated is each and every combination and permutation of genetically modified T cell (i.e., an SAS T cell) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Adoptive transfer of T cells for immunotherapy is highly dependent on the survival of the therapeutic cells post transfer and the ability of the transferred cells to home to tissue bearing the antigen of interest where the effector function of the T cell can result in destruction of the aberrant tissue. Nevertheless, depending on the amount of cells surviving transfer, the desired therapeutic outcome may not be achieved and/or significant long-term protection may not be obtained.

The disclosed compositions and methods that take advantage of the natural T cell response to antigen to produce a long-term supply of antigen and antigen specific T cells (both effector and memory T cells). Specifically, CD8+T-lymphocytes engage in destruction of target cells expressing cognate antigen and concomitantly undergo clonal amplification resulting in generation of more effector cells as well as a few memory cells which can be maintained at stable numbers long term. The disclosed genetically modified T cells provide an antigen of interest as well as a T cell receptor for said antigen (i.e., they are self-antigen specific (also referred to herein as Self-antigen specific T cells (or SAS)). By providing self-Ag specific CD8+ T-cells (SAS Cells) antigen as cellular vaccines supplemented during transfer the engraftment and survival of the therapeutic cells can be enhanced by providing a self-renewing pool of Ag-presenting "vaccine" cells.

Thus, disclosed herein are genetically modified T cells, wherein the T cell has been modified to express one, two, three, four, five, six, seven, eight, nine, ten, or more T cell receptors specific for one, two, three, four, five, six, seven, eight, nine, ten, or more antigens of interest and wherein the T cell comprises one, two, three, four, five, six, seven, eight, nine, ten, or more vectors encoding the one, two, three, four, five, six, seven, eight, nine, ten, or more antigens of interest (i.e. SAS T cells).

The antigen of interest or therapeutic peptide can be any antigen or therapeutic peptide for which increased and prolonged T cell response is sought an effective TCR or CAR response can be raised. For example, the antigen can be an antigen from a tumor, bacteria, or virus.

In one aspect disclosed herein are genetically modified T cells, wherein the antigen of interest is a tumor antigen. For example, the tumor antigen is selected from the group consisting of ALK, BAGE proteins, BIRC5 (survivin), BIRC7, CA9, CALR, CCR5, CD19, CD20 (MS4A1), CD22, CD27, CD30, CD33, CD38, CD40, CD44, CD52, CD56, CD79, CDK4, CEACAM3, CEACAM5, CLEC12A, DEPDC1, EGFR, EGFR variant III, ERBB2 (HER2), ERBB3, ERBB4, EPCAM, EPHA2, EPHA3, FCRL5, FLT3, FOLR1, GAGE proteins, GD2, GD3, GPNMB, GM3, GPR112, IL3RA, KIT, KRAS, LGR5, EBV-derived LMP2, L1CAM, MAGE proteins, MLANA, MSLN, MUC1, MUC2, MUC3, MUC4, MUC5, MUC16, MUM1, ANKRD30A, NY-ESOT (CTAG1B), OX40, PAP, PAX3, PAX5, PLAC1, PRLR, PMEL, PRAME, PSMA (FOLH1), RAGE proteins, RET, RGS5, ROR1, ROS1, SART1, SART3, SLAMF7, SLC39A6 (LIV1), STEAP1, STEAP2, TERT, TMPRSS2, Thompson-nouvelle antigen, TNFRSF17, TYR, UPK3A, VTCN1, WT1, gp72, p53, the ras oncogene product, HPV E7, telomerase, and melanoma gangliosides.

As noted above, the antigen of interest can be a viral antigen. Thus, in one aspect, disclosed herein are genetically modified T cells wherein the T cell has been modified to express one, two, three, four, five, six, seven, eight, nine, ten, or more T cell receptors specific for one, two, three, four, five, six, seven, eight, nine, ten, or more antigens of interest, wherein the T cell comprises one, two, three, four, five, six, seven, eight, nine, ten, or more vectors encoding the one, two, three, four, five, six, seven, eight, nine, ten, or more antigens of interest, and wherein at least one antigen of the one, two, three, four, five, six, seven, eight, nine, ten, or more antigens of interest is a viral antigen. For example, the viral antigen can be from a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Zika virus, Lassa fever virus, Eastern Equine Encephalitis virus, Japanese Encephalitis virus, St. Louis Encephalitis virus, Murray Valley fever virus, West Nile virus, Lymphocytic choriomeningitis virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, Human Immunodeficiency virus type-2; echovirus; parvovirus; vaccinia virus; molluscum virus; JC virus; and arboviral encephalitis virus antigen.

Additionally, as previously stated, the one, two, three, four, five, six, seven, eight, nine, ten, or more antigens of interest can be a bacterial antigen. Thus, in one aspect, disclosed herein are genetically modified T cells wherein the T cell has been modified to express one, two, three, four, five, six, seven, eight, nine, ten, or more T cell receptors specific for one, two, three, four, five, six, seven, eight, nine, ten, or more antigens of interest, wherein the T cell comprises one, two, three, four, five, six, seven, eight, nine, ten, or more vectors encoding the one, two, three, four, five, six, seven, eight, nine, ten, or more antigens of interest, and wherein at least one antigen of the one, two, three, four, five, six, seven, eight, nine, ten, or more antigen of interest are a bacterial antigen. For example, the bacterial antigen can be an antigen selected from a bacterium from the group consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides, Legionella pneumophila, Salmonella typhi, Shigella species, Yersinia pestis, Pasteurella haemolytica, Pasteurella multocida, Actinobacillus pleuropneumoniae, Listeria monocytogenes, Listeria ivanovii, Brucella abortus, Cowdria ruminantium, Chlamydia pneumoniae, Chlamydia trachomatis, Chlamydia psittaci, Coxiella burnetti, Ehrlichia species, Staphylococcus aureus, Staphylococcus epidermidis, Streptococcus pyogenes, Streptococcus agalactiae, Bacillus anthracis, Escherichia coli, Vibrio cholerae, Campylobacter species, Neiserria meningitidis, Neiserria gonorrhea, Pseudomonas aeruginosa, Haemophilus influenzae, Haemophilus ducreyi, Clostridium tetani, Clostridium botulinum, Yersinia enterolitica*, meningococci, *Klebsiella, Proteus, Serratia*, diphtheria, bacilli, leptospira, and Lyme disease bacterial antigen.

It is understood and herein contemplated that in addition to establishing strong and prolonged T cell responses to one, two, three, four, five, six, seven, eight, nine, ten, or more antigens of interest, as a consequence of using T cells with chimeric TCRs or that have been genetically modified to recognize an antigen of interest, a memory T cell pool is generated. Thus, there is a resident pool of cells that can provide long-term production of an antigen, immunosuppressive cytokine, replacement enzyme, or therapeutic peptide encoded on a vector. This antigen production can be used therapeutically to provide a molecule replacement to treat conditions where immunosuppressive cytokine, replacement enzyme, or therapeutic peptide (including peptide hormones) replacement therapy would be a remedy. For example, the providing of erythropoietin (EPO) to treat chronic anemia or the providing of insulin to treat diabetes. Thus, in one aspect disclosed herein are genetically modified T cells wherein the T cell comprises one, two, three, four, five, six, seven, eight, nine, ten, or more vectors encoding an immunosuppressive cytokine, replacement enzyme, or therapeutic peptide (including peptide hormones). In one aspect, the immunosuppressive cytokine, replacement enzyme, or therapeutic peptide (such as a peptide hormone) can be, EPO, glucgon, insulin, TRAIL, alpha galactosidase, alpha glucosidase, Adiponectin, Amylin, Atrial natriuretic peptide, Brain-derived neurotrophic factor, Calcitonin, erythropoietin, Fellutamide, FNDC5, Follicle-stimulating hormone, Ghrelin, Glucagon-like peptide-1, Gonadotropin, Granulocyte colony-stimulating factor, Growth hormone, Growth hormone-releasing hormone, Incretin, Insulin, Leptin, Liraglutide, Obestatin, Pramlintide, Relaxin, β-glucocerebrosidase, or alpha-galactosidase for enzyme replacement.

There are a number of compositions and methods which can be used to deliver nucleic acids such as the antigen of interest to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, transposons, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

In one aspect, the genetically modified T cells wherein the T cell has been modified to express one, two, three, four, five, six, seven, eight, nine, ten, or more T cell receptors specific for one, two, three, four, five, six, seven, eight, nine, ten, or more antigens of interest, wherein the T cell comprises one, two, three, four, five, six, seven, eight, nine, ten, or more vectors encoding the one, two, three, four, five, six, seven, eight, nine, ten, or more antigens of interest, and wherein the vector is a transposon system (such as for example, Sleeping Beauty transposon system or piggyBac transposon system). As used, herein, a transposon system refers to any system incorporating a transposase and inverted terminal repeats. Where a Sleeping Beauty or piggyBac transposon system in indicated, it is understood that the transposon system utilizes the Sleeping Beauty transposase or piggyBac transposase, respectively.

The vectors supplying expression of the antigen of interest typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. The promoters for use with the disclosed genetically modified T cells (i.e., SAS T cells) can be inducible so that the antigen of interest is expressed only when the inducible conditions are met or turned on or off with the supplying of certain conditions. The promoters can also be tissue-specific thus limiting expression to certain tissue. Thus, in one aspect, disclosed herein are genetically modified T cells wherein the T cell has been modified to express a T cell receptor specific for an antigen of interest, wherein the T cell comprises a vector encoding the antigen of interest, and wherein the antigen of interest is operably linked to an inducible promoter or tissue specific promoter. Additionally, the genetically modified T cells disclosed herein can comprise knock-out systems to allow for the permanent or temporary elimination of expression of the gene of interest.

It is understood and herein contemplated that there can be instances where the effector functions of a T cell can be detrimental to a subject receiving said cells or limit the benefit of therapeutic peptide/antigen of interest delivery of the modified cell. Accordingly, in one aspect disclosed herein are modified T cells and methods of using said modified T cells, wherein the T cells lack on or more effector functions, such as, for example cytokine secretion (for example TNF-α, TNF-β, IL-3, and/or IFN-γ) and effector molecules such as Fas-ligand, CD40 ligand, GM-CSF, perforin, and granzyme. The modification of T cells to remove effector function can be accomplished by any method known in the art including, but not limited to siRNA knockdown. In one aspect, the T cells with reduced cytolytic function but having TCR modified to recognize an antigen of interest can have significant effect in autoimmune disorders where the modified T cell competes with endogenous T cells for antigen and thereby reduce the effector activity of the endogenous T cells. Accordingly, in one aspect, disclosed herein are methods of treating an autoimmune disease, wherein the modified T cell has been further modified to have reduced effector T cell function.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

2. Pharmaceutical Carriers/Delivery of Pharamceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

C. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) *Synthetic Peptides: A User Guide*. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett*. 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

In one aspect, it is understood and herein contemplated that the disclosed genetically modified T cells (i.e., SAS T cells) increase engraftment of adoptively transferred cells. Thus, in one aspect, disclosed herein are methods of increasing engraftment of adoptively transferred T cells comprising administering to a subject a genetically modified T cell wherein the T cell has been modified to express a T cell receptor specific for an antigen of interest and wherein the T cell comprises a vector encoding the antigen of interest. In one aspect, the disclosed methods can further comprise the adoptive transfer to the subject T cells that have not been genetically modified (either as an autologous or homologous T cell transfer).

3. Method of Treating a Disease or Condition

One of the problems facing immunotherapy of cancers is the expression of checkpoint inhibitors which prevent the proliferation of tumor specific T cells. By providing tumor specific T cells to a subject that have been genetically modified to express the antigen for which they are specific, the presence of the checkpoint inhibitor is diminished as the transferred T cells are providing the antigen allowing for generation and proliferation of antigen specific effector and memory T cells. Thus, in one aspect disclosed herein are methods of treating a cancer.

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Accordingly, in one aspect disclosed herein are methods of treating a cancer in a subject comprising administering to a subject with a cancer a genetically one, two, three, four, five, six, seven, eight, nine, ten, or more modified T cells wherein the one, two, three, four, five, six, seven, eight, nine, ten, or more T cells have been modified to express one, two, three, four, five, six, seven, eight, nine, ten, or more T cell receptors specific for one, two, three, four, five, six, seven, eight, nine, ten, or more tumor antigens of interest and wherein the T cell comprises one, two, three, four, five, six, seven, eight, nine, ten, or more vectors encoding the one, two, three, four, five, six, seven, eight, nine, ten, or more tumor antigens of interest. In one aspect, at least one, two, three, four, five, six, seven, eight, nine, ten, or more of the tumor antigen or antigens can be selected from the group consisting of ALK, BAGE proteins, BIRC5 (survivin), BIRC7, CA9, CALR, CCR5, CD19, CD20 (MS4A1), CD22, CD27, CD30, CD33, CD38, CD40, CD44, CD52, CD56, CD79, CDK4, CEACAM3, CEACAM5, CLEC12A, DEPDC1, EGFR, EGFR variant III, ERBB2 (HER2), ERBB3, ERBB4, EPCAM, EPHA2, EPHA3, FCRL5, FLT3, FOLR1, GAGE proteins, GD2, GD3, GPNMB, GM3, GPR112, IL3RA, KIT, KRAS, LGR5, EBV-derived LMP2, L1CAM, MAGE proteins, MLANA, MSLN, MUC1, MUC2, MUC3, MUC4, MUC5, MUC16, MUM1, ANKRD30A, NY-ESO1 (CTAG1B), OX40, PAP, PAX3, PAX5, PLAC1, PRLR, PMEL, PRAME, PSMA (FOLH1), RAGE proteins, RET, RGS5, ROR1, ROS1, SART1, SART3, SLAMF7, SLC39A6 (LIV1), STEAP1, STEAP2, TERT, TMPRSS2, Thompson-nouvelle antigen, TNFRSF17, TYR, UPK3A, VTCN1, WT1, gp72, p53, the ras oncogene product, HPV E7, telomerase, and melanoma gangliosides. It is understood that the disclosed treatment methods can also be utilized to inhibit or prevent metastasis. Thus, tumor antigens can include antigens which are only relevant for metastatic cancers and can be administered prophylactically to inhibit or prevent metastasis. Additionally, it is contemplated herein that the disclosed genetically modified T cells can further comprise checkpoint inhibitors of the PD1/PD-L1 interaction including, but not limited to peptides that bind to PD1 or PD-L1 and block said interaction.

In one aspect, because the disclosed genetically modified T cells can be used to provide a long-term supply of a immunosuppressive cytokine, replacement enzyme, or therapeutic peptide, such as, for example a peptide hormone, said peptide hormone can be used to treat a disease or condition (such as chronic kidney disease or diabetes) where insufficient production of the peptide hormone (such as, for example EPO or insulin) causes the disease or condition or increased production of the peptide hormone (such as, for example EPO or insulin) can ameliorate the negative effects of the disease or condition. Thus, in one aspect, disclosed herein are methods of providing long-term delivery of an antigen to a subject comprising administering to a subject a genetically modified T cell wherein the T cell has been modified to express vector encoding immunosuppressive cytokine, replacement enzyme, or therapeutic peptide. In one aspect, the modified T cell can express a TCR, or chimeric antigen receptor specific for a second antigen (such as, for example OVA or THY 1.1) which can be used to maintain a memory T cell pool of T cells expressing the therapeutic peptide, replacement enzyme, or immunosuppressive cytokine. Because said antigens of interest can be used to treat a disease, also disclosed herein are methods of treating chronic kidney disease or diabetes in a subject comprising administering to a subject with chronic kidney disease or diabetes a genetically modified T cell wherein the T cell has been modified to express a T cell receptor specific for EPO (where the disease is chronic kidney disease) or insulin (where the disease is diabetes) and wherein the T cell comprises a vector encoding EPO (where the disease is chronic kidney disease) or insulin (where the disease is diabetes).

It is understood and herein contemplated that the ability of the genetically modified T cells disclosed herein can be utilized to generate antigen specific T cells not just to supply antigens of interest for ongoing conditions or to teat an already existing condition, but may also be used to inhibit or prevent future infections. That is, the genetically modified T cells can be engineered to express and be specific for a viral, bacterial, or tumor antigen in a subject at risk of being infected with the virus or bacteria or at risk for acquiring the cancer. The genetically modified T cell expresses the viral, bacterial, or tumor antigen. The expression of the antigen results in the rapid generation of endogenous effector T cells specific for the antigen. Additionally, because the genetically modified T cells are also modified to have T cell receptors specific for the expressed viral, bacterial, or tumor antigen the specific T cell pool is amplified. All the antigen specific T cells (endogenous and genetically modified) undergo clonal amplification and produce a memory T cell population which provides long term immunological protection against future infections; or in the case of an existing tumor against metastasis; or in the case of a latent infection, against recurrent activation of the latent infection (FIG. 11). Thus, in one aspect, disclosed herein are methods of treating, reducing, inhibiting, and/or preventing a cancerous condition, or a viral or bacterial infection in a subject comprising administering to a subject in risk of said infection a genetically modified T cell, wherein the T cell has been modified to express one, two, three, four, five, six, seven, eight, nine, ten, or more T cell receptors specific for one, two, three, four, five, six, seven, eight, nine, ten, or more tumor, bacterial or viral antigen of interest; wherein the antigen of interest is an antigen from the tumor, bacterium, or virus from which immunological protection is sought; and wherein the T cell further comprises a vector encoding the one, two, three, four, five, six, seven, eight, nine, ten, or more antigens of interest.

It is understood and herein contemplated that the disclosed methods of treating, reducing, inhibiting, and/or preventing a cancerous condition, or a viral or bacterial infection in a subject disclosed herein can be accomplished by administering any of the modified T cells disclosed herein and as described above. However, it is also understood and contemplated herein that the expression of the antigen of interest and the expression of the T cell receptor specific for said antigen of interest do not have to occur in the same T cell, but can occur on different modified T cells (see FIGS. 12, 13, and 14). For example, the methods of treating, reducing, inhibiting, and/or preventing a cancerous condition, or a viral or bacterial infection in a subject can comprise a first modified T cell that comprises an antigen of interest and a second modified T cell comprises a T cell receptor specific for the antigen of interest (FIG. 12) (said antigen being optionally encoded on a vector in the modified T cell). Alternatively, the methods of treating, reducing, inhibiting, and/or preventing a cancerous condition, or a viral or bacterial infection in a subject can comprise a first modified T cell that comprises a first and a second antigen of interest and a second modified T cell comprises a T cell receptor specific for the first or the second of the antigen of interest (FIG. 13) (said antigens being optionally encoded on a vector in the modified T cell). In such instances, the T cell expressing the antigen of interest is killed by the T cell expressing the T cell receptor specific for the antigen of interest. Antigen presenting cells (such as, for example dendritic cells, engulf and break down the antigen of interest expressing T cell and present the antigen of interest to new T cells generating further activated T cells specific for the antigen of interest. Additionally, the T cells modified to express the T cell receptor specific for the antigen of interest proliferate. This leads to a much more robust T cell response to the antigen of interest. Alternatively again, the methods of treating, reducing, inhibiting, and/or preventing a cancerous condition, or a viral or bacterial infection in a subject can comprise a first modified T cell that comprises a first and a second antigen of interest and a T cell receptor specific for the first antigen of interest a second modified T cell comprising the first antigen of interest and a T cell receptor specific for the first antigen of interest (FIG. 14) (said antigens being optionally encoded on a vector in the modified T cells). Here, the activation and proliferation of antigen specific T cells is even more enhanced do the enhanced uptake and cross-presentation of the first and second antigens by professional antigen presenting cells (for example, dendritic cells). Accordingly, in one aspect, disclosed herein are methods of treating, reducing, inhibiting, and/or preventing a cancerous condition, or a viral or bacterial infection in a subject comprising administering to a subject at least two, three, four, five, six, seven, eight, nine, ten, or more modified T cells, wherein at least one first T cell has been modified to express one, two, three, four, five, six, seven, eight, nine, ten, or more T cell receptors specific for a tumor, bacterial, and/or viral antigen of interest and wherein at least one separate second T cell has been modified to express one, two, three, four, five, six, seven, eight, nine, ten, or more tumor, bacterial, and/or viral antigens of interest. In some aspects the first modified T cell can further comprise at least one T cell receptor for at least one of the antigens of interest it expresses. In some aspects, the second modified T cell can express at least one antigen of interest for which its T cell receptor is specific. It is understood and herein contemplated that in some instances the antigen of interest on the second modified T cell can be the same as one of the antigens of interest on the first modified T cell. In still other additional aspects, both the first and second modified T cells can comprise antigens of interest and T cell receptors specific for at least one antigen of interest.

It is understood and herein contemplated that wherein the disease or condition is a bacterial infection, the antigen of interest is an antigen from the bacterium against which protection is sought. Accordingly, disclosed herein are methods of inhibiting a bacterial infection comprising administering to a subject in risk of said bacterial infection comprising administering to the subject a genetically modified T cell, the T cell has been modified to express a T cell receptor specific for a bacterial antigen and wherein the T cell comprises a vector encoding said bacterial antigen; and wherein the bacterial antigen is an antigen selected from a bacterium from the group consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides, Legionella pneumophila, Salmonella typhi, Shigella species, Yersinia pestis, Pasteurella haemolytica, Pasteurella multocida, Actinobacillus pleuropneumoniae, Listeria monocytogenes, Listeria ivanovii, Brucella abortus, Cowdria ruminantium, Chlamydia pneumoniae, Chlamydia trachomatis, Chlamydia psittaci, Coxiella burnetti, Ehrlichia species, Staphylococcus aureus, Staphylococcus epidermidis, Streptococcus pyogenes, Streptococcus agalactiae, Bacillus anthracis, Escherichia coli, Vibrio cholerae, Campylobacter species, Neiserria meningitidis, Neiserria gonorrhea, Pseudomonas aeruginosa, Haemophilus influenzae, Haemophilus ducreyi, Clostridium tetani, Clostridium botulinum, Yersinia enterolitica,* meningococci, *Klebsiella, Proteus, Serratia,* diphtheria, bacilli, leptospira, and Lyme disease bacterial antigen.

It is also understood and herein contemplated that wherein the disease or condition is a viral infection, the antigen of interest is an antigen from the virus against which protection is sought. Accordingly, disclosed herein are methods of inhibiting a viral infection comprising administering to a subject in risk of said viral infection comprising administering to the subject a genetically modified T cell, the T cell has been modified to express a T cell receptor specific for a viral antigen and wherein the T cell comprises a vector encoding said viral antigen; and the antigen of interest is a viral antigen from a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Zika virus, Lassa fever virus, Eastern Equine Encephalitis virus, Japanese Encephalitis virus, St. Louis Encephalitis virus, Murray Valley fever virus, West Nile virus, Lymphocytic choriomeningitis virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, Human Immunodeficiency virus type-2; echovirus; parvovirus; vaccinia virus; molluscum virus; JC virus; and arboviral encephalitis virus antigen.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Transposon-Modified Antigen-Specific T Lymphocytes for Sustained Erythropoietin Delivery In Vivo The development of a cell therapy platform for safe and long-term delivery of peptide hormones in vivo is a significant advance for patients with a variety of hormonal deficiencies. Erythropoietin (EPO) is a peptide hormone which regulates red blood cell production. Insufficient renal production of EPO is a serious complication of chronic kidney disease (CKD) that results in anemia. Anemia of CKD adversely affects quality of life and is associated with poor clinical outcome. EPO replacement therapy in the form of various erythropoiesis stimulating agents (ESAs) came into clinical use in the United States in 1989 and dramatically reduced the need for blood transfusions in patients with anemia of CKD. However, ESA usage is expensive has been associated with increased risk of adverse clinical outcomes including thrombolytic and cardiovascular events in several clinical trials. Clinically used ESAs differ in amino acid sequence and structure from physiologically produced EPO in vivo and they are generally administered at much higher concentrations than those produced under normal physiological conditions. As such, a gene and cell therapy for sustained production of EPO in situ represents an attractive alternative therapeutic strategy because it more closely recapitulates natural hormonal structure and dynamics potentially facilitating a reduction in costs as well as adverse consequences associated with bolus ESA delivery. Researchers have reported viral vector based strategies for transduction of muscular, hepatic, or dermal tissue with constructs driving EPO production. Although these strategies increased hemoglobin concentration, viral vector based approaches have inherent drawbacks related to their immunogenicity, limited control of EPO production afforded by viral construct packaging restraints, and difficulty in reversing the procedure which may require surgical removal of transduced tissue in cases of EPO over production. In the current studies, a non-viral transposon based approach was evaluated for ex vivo engineering T-lymphocytes to produce EPO while aiming to circumvent some of the limitations associated with viral vector mediated gene therapy.

T-lymphocytes are promising candidates for peptide hormone delivery platforms because they can be harvested relatively easily by phlebotomy, efficiently genetically modified ex vivo, stored for future use, and they can enter the memory compartment and can be sustained for many years. Adoptively transferred T-lymphocytes have recently been embraced as a promising therapeutic platform in oncology. A prerequisite for cell based adoptive transfer therapy is survival and engraftment of the therapeutic cells, processes that are augmented in the presence of cognate antigen. T-lymphocytes specific for antigens presented by latent viral infections such as Epstein-Barr virus (EBV) persist for many years after adoptive transfer. For this reason, antigen specific T cells, such as EBV-specific T lymphocytes, can represent a useful platform for sustained systemic hormone delivery.

Previous studies have established the utility of non-viral transposon systems such as piggyBac for efficient T cell genome modification. Several features of transposon systems make them attractive tools for generating cell therapy platforms including potentially reduced immunogenicity compared to viral vectors and capacity for multi-gene insertion that is facilitated by the relatively large cargo capacity and ability to deliver multiple constructs to a single cell. Another transposon system, Sleeping Beauty, is currently approved for use in human clinical trials aimed at engineering T cells to target CD19-positive B cell malignancies for immunotherapy. A non-viral transposon system was leveraged to develop a safe and efficient T cell based platform for in vivo delivery of therapeutic peptides such as EPO. In these studies, the feasibility of using antigen specific CD8+ T-lymphocytes to deliver EPO long term was demonstrated in an animal model and data was provided supporting the use of EBV-specific T lymphocytes for regulated EPO expression from human T cells.

a) Results (1) Transposon Modification of Mouse T-Lymphocytes

A series of piggyBac vectors were engineered for genetic modification of T cells to enable tracking of lymphocytes, quantitation of their persistence in vivo, and to express both murine and human EPO (FIG. 1). Murine CD8+ lymphocytes were genome modified with the pT-effluc-thy1.1 transposon, confirmed luciferase expression from transferred cells by bioluminescent imaging, and observed thy1.1 expression by flow cytometry. It was observed that ~35% of the cells were transgene positive after 24 hours of in culture (FIG. 2A).

(2) Subdermal Plasmid Vaccine Facilitates Recruitment and Boosting of Adoptively Transferred T-Lymphocytes Luciferase modification enabled the ability to track T cells in vivo, quantitate their ability to persist long-term after adoptive transfer, and to evaluate various vaccination strategies to identify those that best produce long-term cell engraftment and transgene expression. To this end, OT-1 T-cells that express a transgenic T cell receptor (TCR) were used for a peptide fragment derived from chicken ovalbumin (SIINFEKL)(SEQ ID NO: 2) presented on H2-K$^b$ MHC class I, and SIINFEKL as the vaccine antigen. A plasmid based vaccination strategy designed to provide efficient antigen presentation to transferred lymphocytes was evaluated.

To assess the response to vaccination, pT-effluc-thy1.1 transposon modified CD8+ cells were adoptively transferred and tracked engraftment by in vivo bioluminescence imaging. Transposon vaccines have been shown to produce sustained antigen expression and improved antigen-specific T cell responses in vivo. The Sleeping Beauty system was chosen for the vaccine, to avoid inducing an immune response to the piggyBac transposase, which was used for T cell modification to enable long-term transgene expression. Sub-dermal (s.d.) route for vaccine delivery was tested by injecting a plasmid mixture containing pTSB-CAG-OVA transposon and the hyperactive pCMV-SB100X transposase (FIG. 1), complexed with in vivo-jetPEI transfection reagent into the flank of a C57/B16 mice immediately after infusion of OT-1 CD8+ T cells (FIG. 2B). Recruitment of adoptively transferred luciferase positive cells to the vaccine site was observed (FIG. 2C). This response was transient with a peak response at 72 hours followed by luciferase signal decay, presumably as OVA expressing cells are cleared from the site by cytotoxic OVA specific CD8+ T cells. A second booster vaccine administered 10 days after initial adoptive cell transfer (ACT) was effective in further recruiting transferred lymphocytes to the secondary vaccine site indicating persistence of functionally competent, genome modified T cells (FIG. 2C). Although the subdermal vaccine appeared to be effective, alternative, more potent strategies were sought to boost long-term engraftment and transgene expression.

(3) Intravenous T Cell Vaccine Promotes Initial Engraftment of Adoptively Transferred T-Lymphocytes To further augment engraftment and survival, a vaccination approach was developed relying on transposon based genome modification of CD8+ T cells with the pTSB-CAG-OVA transposon construct instead of the subdermal vaccine. In this model, OVA expressing OT-1-T lymphocytes was co-administered i.v. at a 1:20 ratio to the therapeutic effector cells (FIG. 3A). This unique vaccination strategy can produce a stable lymphotropic cellular vaccine that provides prolonged OT-1 T cell stimulation and augment engraftment and persistence. Indeed, a significantly enhanced engraftment of OT-1-specific cells transferred concomitantly with the i.v. OVA-T cell vaccine was observed compared to cells transferred and stimulated with two consecutive subdermal plasmid vaccines, as determined by whole animal luminescence (FIG. 3B). An increase in luciferase expression was observed as analyzed by area under the curve when comparing the i.v. cellular vaccine to the s.d. vaccine (FIGS. 3C and D, 65% increase, p=0.033) over a period of 60 days. Therefore, the cellular vaccination approach was used for in vivo long-term transgene expression from antigen-specific T cells.

(4) Repeated T Cell Booster Vaccine Administration Promotes Persistence of Adoptively Transferred T-Lymphocytes To produce a greater magnitude of expansion and persistence of the adoptively transferred T cells, the utility of repeated boosts with a T cell-OVA vaccine was evaluated. For these studies wild type C57/B16 T-lymphocytes transiently transfected ex vivo with an OVA antigen expression construct (pTSB-CAG-OVA) were used to provide a booster vaccination. The T cell-OVA vaccine was transferred by intraperitoneal (i.p.) injection to wild type C57/B16 mice that had previously received i.v. infusions of pT-effluc-thy1.1 modified OT-1 cells in combination with OT-1-OVA+ T cells as described above (FIG. 4A). Bioluminescent imaging indicated that this vaccination strategy produced robust recruitment of genome modified adoptively transferred OT-1 lymphocytes to the vicinity of the injection site. Importantly, this vaccination approach facilitated potent re-boosting of adoptively transferred cells upon repeated administration (FIG. 4B). In mice that underwent i.v. T cell vaccine at the time of ACT, efficient boosting of transferred cells by the i.p. cellular vaccine approach was observed as long as 300 days after initial transfer (FIG. 4C). This indicates that transgene expression from antigen-specific T cells that were administered using the approach can be re-boosted at least 300 days after adoptive transfer.

(5) Long-Term Delivery of EPO by Adoptively Transferred T-Lymphocytes

To determine if antigen-specific T cells could mediate therapeutic protein delivery in vivo, EPO was overexpressed in wild type mice with a normal hematocrit. A raise in hematocrit means that sufficient EPO was expressed to increase hematocrit above normal levels. A murine EPO expressing transposon (pT-EF1α-mEPO (FIG. 1)) was engineered and tested its ability to raise the hematocrit in mice following hydrodynamic tail vein injection. As expected, severe polycythemia resulted as the hematocrit rose to over 80% (FIG. 5). A tetracycline inducible expression system was used to express mEPO from mouse liver following hydrodynamic tail vein injection. Although this inducible system was able to prevent severe polycythemia, there was some expression leak indicated by an elevation in hematocrit observed prior to doxycycline administration (FIG. 5). Although hydrodynamic tail vein injection allowed us to test the EPO transposons in vivo, clinical translatability of this approach to humans is unclear.

Next the strategy was evaluated to determine if using antigen-specific T cells in vivo for therapeutic protein delivery by transferring EPO expressing T cells to wild type mice (FIG. 6A). For these studies OT-1 lymphocytes were harvested and genome modified them to stably produce mEPO from the constitutive EF1α-promoter (FIG. 1) before adoptively transferring the cells into adult mice. Advantage was taken of the T cell vaccine approach to establish the feasibility of producing EPO and raising the hematocrit in vivo. The amount of mEPO delivered by transposon modified T lymphocytes was determined by monitoring plasma mEPO concentration following adoptive transfer (FIG. 6B). $2 \times 10^7$ OT-1 lymphocytes were transferred in by tail vein injection in conjunction with the i.v. OT-1/OVA T cell vaccine. A mean plasma mEPO concentration of 4405 ng/ml 24 hours was observed after adoptive transfer (compared to a mean plasma concentration of 193 ng/ml in untreated mice). Four weeks after ACT plasma mEPO concentration fell to a mean of 546 ng/ml. In order to determine the plasma mEPO concentration elicited by the i.p. cellular vaccine the vaccine was administered on day 41 after ACT and observed a mean plasma mEPO concentration of 2312 ng/ml 24 hours after vaccination. Importantly, the infusion of mEPO producing T cells resulted in an elevation of HCT in wild type (non-anemic) mice measured at 42 days (FIG. 6C).

Next an evaluation was made as to whether hematocrit could be increased beyond 6 weeks in WT mice. $2 \times 10^7$ OT-1 lymphocytes were transferred in by tail vein injection in conjunction with the i.v. OT-1/OVA T cell vaccine. On days 7 and 14 after ACT, i.p. T cell vaccination were performed and monitored hematocrit periodically (FIG. 7A). A 33% elevation in hematocrit was observed by week 5 after transfer (FIG. 7B). The hematocrit remained significantly elevated above pre-transfer levels for more than 10 weeks without progressing to severe polycythemia. The i.p. cellular vaccination protocol was then repeated on weeks 12 and 13 effectively boosting hematocrit which was maintained at an elevated state until at least 20 weeks after initial ACT (FIG. 7B). These results support the utility of using adoptively transferred antigen-specific T cells as a platform for sustained EPO delivery.

The observations were extended to determine if our T-lymphocyte based method of EPO delivery could effectively reverse anemia of chronic kidney disease in the adenine nephrotoxicity model. For this study mice were challenged with an adenine diet regimen which lead to anemia (FIG. 7C). Anemic mice were then administered 2×10⁷ EF1α-mEPO transposon modified T-lymphocytes and hematocrit was assessed every two weeks. Treated mice achieved hematocrit within the normal range (~42) by two weeks post ACT and maintained at these levels for at least 6 weeks (FIG. 7C). These results indicate that ACT with mEPO modified T-lymphocytes is an effective method of correcting anemia in an animal model.

(6) Modification of EBV-Specific Human T-Lymphocytes for Regulated Production and Secretion of hEPO The ability of engineered antigen-specific mouse T cells to express EPO in vivo and to raise hematocrit long-term led to the efforts to modify human antigen-specific T cells to express EPO. The piggyBac transposon system to modify the genome of EBV-specific T cells. Next it was determined whether EPO-modified EBV-specific T cells retained antigen specificity. In consideration of possible future clinical application, an inducible system was developed for regulation of EPO expression and hematocrit levels that can be shut off if needed. A variety of systems have been developed to allow for drug-inducible gene expression. In these studies the potential for regulated expression of recombinant human EPO in EBV-specific T cells was evaluated using the tetracycline response system. EBV-specific lymphocytes were genome modified with the pT-tight-hEPO transposon (FIG. 1). EPO production and secretion by the EBV specific T cells in the presence and absence of tetracycline was monitored by quantifying culture media EPO content using an ELISA assay. Similar levels of EPO were observed in the culture supernatants from mock-transfected EBV lymphocytes and from pT-tight-hEPO modified lymphocytes in the absence of added tetracycline. However, robust induction of EPO secretion into the cell culture supernatants was observed from pT-tight-hEPO modified cells in the presence of 1 µg/ml tetracycline (FIG. 8A). hEPO expression was evaluated by Western blot comparing hEPO produced from a human T cell line to that of Chinese hamster ovary (CHO) cells which have previously been used to produce EPO and other therapeutic proteins. Transfection of the same hEPO producing vector (pT-tight-hEPO) into human Jurkat T cells when compared to CHO cells resulted in a different migration upon gel electrophoresis. Therefore, post-translational modification of hEPO produced from human T cells can differ from that in other cell types. Nonetheless, these results indicate that the Tet-ON tetracycline response system allows for tightly regulated production and secretion of EPO in EBV specific T cells.

Previous reports have demonstrated the long-term persistence of genome modified EBV-specific T cells in vivo revealing them to be a possible long-term cellular delivery vehicle for peptide hormones such as EPO. The utilization of EBV specific lymphocytes for EPO delivery is predicated on the idea that these cells retain target specificity after in vitro expansion and genome modification. Using a lactate dehydrogenase (LDH) release cytotoxicity assay, it was shown that EPO modified EBV specific T cells do indeed retain target specificity (FIG. 8B), killing autologous, but not HLA mismatched EBV-transformed B lymphoblastoid cell lies (LCLs). Therefore, human antigen (EBV−) specific T cells can be genome modified to express EPO and retain their antigen specificity.

b) Methods (1) Vectors

The plasmid vectors pT-effluc-thy1.1, pCMV-m7pB, and pCMV-SB100X are used herein. The pT-EF1α-mEPO was synthesized by Cyagen Biosciences (Santa Clara, Calif.). The pTSB-CAG-OVA vector to encode a kozak consensus sequence followed by the nine amino acid peptide sequence corresponding to chicken ovalbumin residues 257-264 and a stop codon (5'GATCGCCACCATGAGTATAAT-CAACTTTGAAAAACTGTAACCGG)(SEQ ID NO: 1) by replacing the piggyBac terminal repeats (TRs) in pT-CA-GLuc (30) with the Sleeping Beauty TRs and swapping out the luciferase cDNA for the OVA peptide. The vector pT-Tight-hEPO was generated by blunt cloning the Tet-ON element from pT-Tet-ON (Clontech, Mountain View Calif.) into the multiple cloning site (MCS) of the zeo-pT-MCS vector to make zeo-pT-MCS-Tet-ON. The TRE-hEPO element was cloned into the XhoI site of zeo-pT-MCS-Tet-ON generating TRE-hEPO-MCS-Tet-ON. The 250 bp core insulator sequence was synthesized from the chicken B-globin 5'HS4 element with flanking AscI and AgeI sites (Genescript, NJ). This was then cloned into the MCS of the zeo-pT-TRE-hEPO-MCS-Tet-ON vector to generate pT-Tight-hEPO. All plasmid vectors were confirmed by DNA sequencing.

(2) Animals

Wild type C57/B16 mice, albino C57/B16 mice (B6-Tyr$^{c-2J}$), and OT-1 TCR transgenic mice harboring T-lymphocytes that recognize the MHC-I (H-2K$^b$) restricted epitope of chicken ovalbumin$_{257-264}$ (SIINFEKL) were obtained from Jackson Labs. Anemia was induced by adenine diet as described. Briefly, animals were fed LabDiet 5001 (St. Louis, Mo.) supplemented with 0.25% adenine ad libitum for 2 weeks followed by one week on normal adenine free chow (LabDiet 5001, St. Louis, Mo.) and then one additional week on 0.25% adenine chow before maintaining mice on adenine free chow for the duration of the study. All animal experiments were approved by the Institutional Animal Care and Use Committee of Vanderbilt University Medical Center.

(3) Adoptive Transfers and Vaccines

Lymphocytes for adoptive transfer and cellular vaccine preparation were harvested from adult mouse spleens. Lymphocytes were isolated from whole spleen by crushing against 70 um mesh with the back of a sterile 10 ml syringe plunger and washing once with PBS before pelleting cells by spinning at 300 g for 5 minutes. The cells were suspended in PBS and lymphocytes were isolated using lympholyte cell separation medium (Cedarlane, Burlington N.C.) according to the manufacturer's instructions. CD8+ lymphocytes were purified from the mixed lymphocyte preparation using the MACS mouse CD8a+ T cell isolation Kit (Miltenyi Biotec, Auburn Calif.). Purified CD8+ lymphocytes were then expanded in complete T cell medium (Advanced RPMI containing 10% FBS) supplemented with IL2 [10 ng/ml] (Peprotech, Rocky Hill N.J.) and anti-CD3e [2.5 µg/ml] (Fisher Scientific, Hampton N.H.) for 3 days resulting in 7-10 fold expansion in cell numbers. After in vitro expansion the cells were washed briefly in PBS by centrifugation and transfected with the Neon (Life Technologies, Grand Island N.Y.) transfection system according to manufacturer instructions for mouse T cells. Cellular vaccines were generated by transfecting in vitro expanded T cells with a mixture of 5 µg pCMV-SB100X and 25 µg pTSB-CAG-OVA in the case of the i.v. vaccine and 25 µg pTSB-CAG-OVA in the case of the i.p. vaccine. Subdermal plasmid vaccines were prepared by mixing 5 µg pTSB-CAG-OVA and 1 µg pCMV-SB100X with in vivo-jetPEI (Polyplus, New York N.Y.) according to manufacturer's instructions. Dorsal flanks were shaved and 30 µl of vaccine mixture was injected subdermally using an insulin syringe. In vitro expanded OT-1 T cells were prepared for adoptive transfer by transfection with 5 µg pCMV-M7PB and 25 µg of pT-effluc-thy1.1 or 25 µg of pT-EF1a-mEPO.

Prior to adoptive transfer, mice were preconditioned by exposure to 5 gy of lymphodepleting radiation using a cesium irradiator. T cells were transfected as described above, allowed to recover in complete T cell media for 1.5 hrs and then adoptively transferred via tail vein injection. 30 µl of the plasmid vaccine mixture was transferred by subdermal injection to the shaved flank of recipient mice using a 28 gauge needle. Intra venous T cell vaccines were prepared by transfecting CD8+OT-1 T cells as described above mixed at a ratio of 19:1 with the pT-effluc-thy1.1 or pT-EF1α-mEPO respectively and co-administered during adoptive transfer. i.p. T cell vaccines were prepared by transfection of in vitro expanded CD8+ T cells with 25 µg pTSB-CAG-OVA using the Neon transfection system washed and suspended in PBS at $1 \times 10^6$ cells/ml and 0.1 ml was immediately transferred into recipient mice by i.p. injection.

(4) Bioluminescent Imaging

Mice were anesthetized using isoflurane and injected i.p. with 100 µg luciferin substrate (Perkin Elmer, Waltham, Mass.) in PBS. Approximately 10 minutes after luciferase injections mice were imaged on the Xenogen IVIS 200 (Perkin Elmer, Waltham, Mass.). All data shown represent mean luminescence observed by summing dorsal and ventral measurements obtained from identical ROIs drawn over the trunk and head of each individual mouse.

(5) Assessment of Hematocrit

Blood was collected in Microvette CB300 LH Lithium-Heparin collection tubes (Sarstedt, Newton N.C.) by saphenous vein bleeding. Hematocrit was measured using the FORCYTE Hematology Analyzer (Oxford Science, Oxford Conn.).

(6) Quantification of EPO Expression Using Enzyme-Linked Immunosorbant Assay (ELISA)

Plasma mouse EPO levels were quantified by ELISA (R&D Systems, Minneapolis, Minn.) according to manufacturer instructions. Blood was obtained by saphenous vein bleed into heparinized Microvette CB300 LH Lithium-Heparin collection tubes (Sarstedt, Newton, N.C.) and plasma was harvested by immediately centrifuging blood at 1500×g for 5 min and stored at −80° C. EPO concentration was determined using Human EPO Platinum ELISA kit (eBiosciences, Waltham, Mass.) according to manufacturer's instructions. Plates were read on a Fluostar Omega plate reader (BMG Labtech, Cary N.C.).

(7) Lactate Dehydrogenase (LDH)-Release Cytotoxicity Assay

Cytotoxicity measurements were performed using Cytotox-96 Kit (Promega, Madison Wis.). Breifly, 10,000 EBV LCLs (target cells) were incubated with the indicated number of effector T cells for 4 hours in a humidified incubator at 37 C in 5% $CO_2$. Lysis of the target cells by effectors leads to LDH release, which is measured by conversion of tetrazolium salt to a red formazan product detected at 490 nm on a Fluostar Omega.

(8) Flow Cytometry 24 hours after transfection 1 million cells were collected and stained with BB515 labelled anti-mouse thy1.1 antibodies (BD564607, Fisher Scientific, Hampton N.H.) and acquired on a LSRFortessa (BD Biosciences, San Jose Calif.) cytometer.

(9) Generation and Genome Modification of Human EBV-Specific T-Cells

EBV-lymphoblastoid cell lines (LCLs) were generated. Peripheral blood mononuclear cells (PBMCs) were prepared from blood samples obtained from healthy donors under informed consent using ficoll density centrifugation. T cells were cultured in T cell media (TCM) containing Advanced RPMI (Invitrogen, USA) supplemented with 10% FCS and 2 mM L-GlutaMAX-1 (Invitrogen, USA). PBMCs were incubated overnight with 10 ng/ml of IL-7 (eBiosciences, Fisher, Waltham, Mass.). Cells were harvested the next day and nucleofected with 5 µg of each vector using the Human T cell Nucleofector Kit (Lonza, Basel, Switzerland) and Amaxa nucleofector device (program U-014, unstimulated T cells). The nucleofected PBMCs were rested overnight in complete T-cell media with 10 ng/ml IL-7 and 1000 U/ml of IL-4 (eBiosciences, Fisher, Waltham, Mass.). PBMCs were then stimulated with 40 gy irradiated auto-LCLs at a ratio of 40:1 for 8 days. On day 11, cells were resusprended at a ratio of 4:1 with irradiated auto-LCLs. On day 20, ihepo-CTLs were enriched by magnetic selection using a MACS human CD19+ cell enrichment kit according to manufacturer's instruction on an LS column (Miltenyi Biotec, Auburn, Calif.).

c) Discussion

Herein is shown that antigen-specific T cells can be used as a cellular vehicle for long-term peptide hormone therapy. EPO was used as the peptide hormone of choice given the ease of measurement of biological readout of EPO levels raising hematocrit in vivo, and the medical need for this peptide in patients with anemia. The piggyBac transposon system was used for non-viral genetic modification of T cells because of its proven use in human T cells and other clinically relevant cell populations. The ability to perpetuate the persistence of transposon-modified antigen-specific mouse T cells in vivo using vaccination was demonstrated herein, and then this strategy was used to raise the hematocrit long-term in vivo via EPO transgene expression. The study was extended by demonstrating that human antigen (EBV)-specific T cells can be modified to inducibly express EPO and retain their antigen specificity.

A previous report demonstrated delivery of hEPO using antigen-specific B lymphocytes Eµ- and Igλ-based hEPO expressing transgenic mice. To determine if T cells were a viable EPO delivery platform, it was first verified that they can undergo genome modification and stably secrete functional hormone after adoptive transfer. The OT-1 transgenic TCR model was utilized for these studies because these cells harbor predetermined antigen specificity providing the opportunity to elicit TCR engagement facilitating amplification and stable engraftment in vivo by various vaccination models. During the course of these studies an effective cellular vaccine approach was identified which takes advantage of several unique characteristics of T cells. These studies were extended using T cells as the cellular vaccine platform with the ultimate goal of peptide hormone delivery. Indeed, augmented engraftment and persistence of T cells was observed when ACT preparations were "spiked" with a vaccine of stably genome modified, OVA antigen expressing OT-1 CD8+ T cells. This enhanced engraftment coupled with an i.p. cellular vaccination booster strategy provided sufficient EPO modified T cell engraftment and persistence to affect hematocrit for up to four months after ACT. Cross presentation can be the primary mechanism by which T cells modified to express antigenic peptides provide effective vaccination.

The key to delivering EPO long-term via cell therapy is to facilitate efficient, stable, long term engraftment of EPO producing cells. EBV-specific CD8+ T cells were evaluated as a platform for EPO delivery because these cells can be efficiently expanded in vitro and because they respond to antigenic stimulation by latent viral infection in vivo undergoing expansion and resulting in stable persistence in vivo.

The results demonstrate the feasibility of modifying in vitro expanded EBV lymphocytes to produce EPO under the tight control of a tetracycline response element without compromising the functional target specificity required to facilitate engraftment and persistence after autologous transfer into a host with latent EBV infection.

Genetically modified antigen-specific T cells represent an attractive platform for long-term cellular delivery of therapeutic peptides. Antigen-specific T cells are more terminally differentiated than stem cell populations making them a safer alternative for genome modification. The T cell population can be re-boosted via vaccination with cognate antigen resulting in re-boosting of protein production. Alternatively, an inducible expression system can be used to more tightly regulate protein production from these cells as was demonstrated herein with human T cells. The safety of such cells can be improved through co-administration of an inducible suicide gene, which can also be introduced into human T cells using the piggyBac system. The results indicate that antigen-specific T cells represent a viable platform for long-term therapeutic delivery of EPO and possibly other peptide hormones.

As shown in FIG. 9, perforin mediated cytolytic function enhances antigen trafficking to lymph nodes (LN). Each mouse underwent adoptive transfer with 4 million OT-1 CD8+ T cells obtained from either Perforin-null donors (bottom panel) or Perforin-WT donors (top panel) along with a cellular vaccine consisting of 500,000 OT1 T cells transposon modified to express OVA peptide. Panels on left show luciferase signal 35 days after initial adoptive transfer. By 42 days after initial adoptive transfer the luciferase signal was below the level of detection in both groups. After the imaging on day 42 each mouse was given an i.p. injection containing 100,000 wild-type C57B16 CD8+ T cells transfected with a plasmid driving expression of OVA peptide. We observe a localized reaction by luciferase modified OT-1 T cells at the site of the ip injection indicating that some of the initially transferred luciferase modified OT1 cells are still present and competent to respond to stimulation by antigen. A pronounced enhancement of modified T cell expansion/recruitment to the cervical LN in the was observed Perforin-WT group. Conversely, despite a response at the local booster injection site, pronounced recruitment to LNs was not observed in the mice initially transferred with OT-1 T cells obtained from Perforin-null donors. This supports the hypothesis that cytolytic cell function enhances antigen transport and presentation within the LNs (right three panels). All images were normalized as indicated by the scale bar to the right. This figure is important because it provides evidence that lysis of T cells expressing antigenic peptide leads to enhanced antigen cross presentation within lymphatics. Additionally, as shown in FIGS. 10A and 10B, the self-antigen-specific T cell vaccine leads to superior engraftment of luciferase modified T cells when compared to subdermal plasmid vaccine.

E. References

Babitt J L & Lin H Y (2012) Mechanisms of anemia in CKD. *Journal of the American Society of Nephrology*, 23(10): 1631-1634.

Bear A S, Cruz C R, & Foster A E (2011) T cells as vehicles for cancer vaccination. *Journal of biomedicine & biotechnology* 2011:417403.

Bertino P, et al. (2014) Vaccination with a piggyBac plasmid with transgene integration potential leads to sustained antigen expression and CD8(+) T cell responses. *Vaccine* 32(15):1670-1677.

Besarab A, et al. (1998) The effects of normal as compared with low hematocrit values in patients with cardiac disease who are receiving hemodialysis and epoetin. *N Engl J Med* 339(9):584-590.

Blum S, et al. (2017) TARGT Gene Therapy Platform for Correction of Anemia in End-Stage Renal Disease. *N Engl J Med* 376(2):189-191.

Clarke S R, et al. (2000) Characterization of the ovalbumin-specific TCR transgenic line OT-I: MHC elements for positive and negative selection. *Immunology and cell biology* 78(2):110-117.

Di Stasi A, et al. (2011) Inducible apoptosis as a safety switch for adoptive cell therapy. *N Engl J Med* 365(18): 1673-1683.

Doherty J E, et al. (2012) Hyperactive piggyBac Gene Transfer in Human Cells and In Vivo. *Human Gene Therapy* 23(3):311-320.

Doherty J E, Woodard L E, Bear A S, Foster A E, & Wilson M H (2013) An adaptable system for improving transposon-based gene expression in vivo via transient transgene repression. *FASEB J.* 27(9):3753-3762.

Drueke T B, et al. (2006) Normalization of hemoglobin level in patients with chronic kidney disease and anemia. *N. Engl. J. Med.* 355(20):2071-2084.

Fesnak A D, June C H, & Levine B L (2016) Engineered T cells: the promise and challenges of cancer immunotherapy. *Nature reviews. Cancer* 16(9):566-581.

Foster A E, et al. (2008) Antitumor activity of EBV-specific T lymphocytes transduced with a dominant negative TGF-beta receptor. *Journal of immunotherapy* 31(5):500-505.

Galvan D L, et al. (2015) Anti-Tumor Effects after Adoptive Transfer of IL-12 Transposon-Modified Murine Splenocytes in the OT-I-Melanoma Mouse Model. *PLoS One* 10(10):e0140744.

Gao G, et al. (2004) Erythropoietin gene therapy leads to autoimmune anemia in macaques. *Blood* 103(9):3300-3302.

Heslop H E (2009) How I treat EBV lymphoproliferation. *Blood* 114(19):4002-4008.

Heslop H E, et al. (1996) Long-term restoration of immunity against Epstein-Barr virus infection by adoptive transfer of gene-modified virus-specific T lymphocytes. *Nat Med* 2(5):551-555.

Hoppe P S, Coutu D L, & Schroeder T (2014) Single-cell technologies sharpen up mammalian stem cell research. *Nature cell biology* 16(10):919-927.

Johnston J, et al. (2003) Regulated expression of erythropoietin from an AAV vector safely improves the anemia of beta-thalassemia in a mouse model. *Molecular therapy*, 7(4):493-497.

Kahlig K M, et al. (2010) Multiplexed transposon-mediated stable gene transfer in human cells. *Proceedings of the National Academy of Sciences of the United States of America* 107(4):1343-1348.

Kebriaei P, et al. (2016) Phase I trials using Sleeping Beauty to generate CD19-specific CAR T cells. *The Journal of clinical investigation* 126(9):3363-3376.

Koury M J & Haase V H (2015) Anaemia in kidney disease: harnessing hypoxia responses for therapy. *Nature reviews. Nephrology* 11(7):394-410.

Mocini D, Leone T, Tubaro M, Santini M, & Penco M (2007) Structure, production and function of erythropoietin: implications for therapeutical use in cardiovascular disease. *Curr. Med. Chem.* 14(21):2278-2287.

Nakazawa Y, et al. (2009) Optimization of the PiggyBac transposon system for the sustained genetic modification of human T lymphocytes. *Journal of immunotherapy* 32(8):826-836.

Nakazawa Y, et al. (2013) Evaluation of Long-term Transgene Expression in piggyBac-Modified Human T Lymphocytes. *Journal of Immunotherapy* 36(1):3-10.

Osada S, et al. (1999) Gene therapy for renal anemia in mice with polycystic kidney using an adenovirus vector encoding the human erythropoietin gene. *Kidney Int* 55(4):1234-1240.

Pfeffer M A, et al. (2009) A trial of darbepoetin alfa in type 2 diabetes and chronic kidney disease. *N. Engl. J. Med.* 361(21):2019-2032.

Rooney C M, et al. (1998) Infusion of cytotoxic T cells for the prevention and treatment of Epstein-Barr virus-induced lymphoma in allogeneic transplant recipients. *Blood* 92(5):1549-1555.

Russo V, et al. (2007) Lymphocytes genetically modified to express tumor antigens target DCs in vivo and induce antitumor immunity. *The Journal of clinical investigation* 117(10):3087-3096.

Saridey S K, et al. (2009) PiggyBac Transposon-based Inducible Gene Expression In Vivo After Somatic Cell Gene Transfer. *Molecular Therapy* 17(12):2115-2120.

Saridey S K, et al. (2009) PiggyBac transposon-based inducible gene expression in vivo after somatic cell gene transfer. *Molecular therapy,* 17(12):2115-2120.

Scholler J, et al. (2012) Decade-long safety and function of retroviral-modified chimeric antigen receptor T cells. *Sci Transl Med* 4(132):132ra153.

Shapir N, et al. (2015) Preclinical and Preliminary Clinical Evaluation of Genetically Transduced Dermal Tissue Implants for the Sustained Secretion of Erythropoietin and Interferon alpha. *Human gene therapy. Clinical development* 26(4):216-227.

Skali H, et al. (2011) Stroke in patients with type 2 diabetes mellitus, chronic kidney disease, and anemia treated with Darbepoetin Alfa: the trial to reduce cardiovascular events with Aranesp therapy (TREAT) experience. *Circulation* 124(25):2903-2908.

Smith C A, et al. (1995) Production of genetically modified Epstein-Barr virus-specific cytotoxic T cells for adoptive transfer to patients at high risk of EBV-associated lymphoproliferative disease. *Journal of hematotherapy* 4(2):73-79.

Takacs K, et al. (2004) The regulated long-term delivery of therapeutic proteins by using antigen-specific B lymphocytes. *Proc Natl Acad Sci USA* 101(46):16298-16303.

Woodard L E & Wilson M H (2015) piggyBac-ing models and new therapeutic strategies. *Trends Biotechnol* 33(9):525-533.

---

---

What is claimed is:

1. A method of increasing engraftment of adoptively transferred T cells comprising administering to a subject a genetically modified T cell, wherein the T cell has been modified to express a T cell receptor specific for an antigen of interest and wherein the T cell comprises a vector encoding the antigen of interest for which the T cell receptor is specific.

2. A method of increasing engraftment of adoptively transferred T cells comprising administering to a subject a first T cell genetically modified to express a T cell receptor specific for an antigen of interest and a second T cell genetically modified to express a vector encoding the antigen of interest for which the T cell receptor of the first T cell is specific.

* * * * *